US009097730B2

(12) United States Patent
Diwu et al.

(10) Patent No.: US 9,097,730 B2
(45) Date of Patent: Aug. 4, 2015

(54) FLUORESCEIN LACTONE ION INDICATORS AND THEIR APPLICATIONS

(75) Inventors: Zhenjun Diwu, Sunnyvale, CA (US); Jinfang Liao, Foster City, CA (US)

(73) Assignee: AAT Bioquest, Inc., Sunnyvale, CA (US)

( * ) Notice: Subject to any disclaimer, the term of this patent is extended or adjusted under 35 U.S.C. 154(b) by 230 days.

(21) Appl. No.: 13/374,967

(22) Filed: Jan. 25, 2012

(65) Prior Publication Data

US 2012/0183986 A1 Jul. 19, 2012

Related U.S. Application Data

(60) Continuation-in-part of application No. 12/932,683, filed on Mar. 2, 2011, now Pat. No. 8,779,165, which is a division of application No. 12/040,753, filed on Feb. 29, 2008, now abandoned.

(60) Provisional application No. 60/923,452, filed on Apr. 13, 2007.

(51) Int. Cl.
| | |
|---|---|
| *G01N 33/52* | (2006.01) |
| *G01N 33/84* | (2006.01) |
| *C07D 219/06* | (2006.01) |
| *C07D 311/90* | (2006.01) |
| *C07D 493/10* | (2006.01) |
| *G01N 33/533* | (2006.01) |

(52) U.S. Cl.
CPC .............. *G01N 33/84* (2013.01); *C07D 219/06* (2013.01); *C07D 311/90* (2013.01); *C07D 493/10* (2013.01); *G01N 33/533* (2013.01); *C07C 2103/24* (2013.01)

(58) Field of Classification Search
None
See application file for complete search history.

(56) References Cited

U.S. PATENT DOCUMENTS

| | | | |
|---|---|---|---|
| 4,603,209 A | 7/1986 | Tsien et al. | |
| 4,849,362 A | 7/1989 | DeMarinis | |
| 4,945,171 A | 7/1990 | Haugland et al. | |
| 5,049,673 A | 9/1991 | Tsien et al. | |
| 5,134,232 A | 7/1992 | Tsien et al. | |
| 5,227,487 A | 7/1993 | Haugland et al. | |
| 5,380,836 A | 1/1995 | Rogart | |
| 5,405,975 A | 4/1995 | Kuhn et al. | |
| 5,436,128 A | 7/1995 | Harpold et al. | |
| 5,439,828 A | 8/1995 | Masilamani et al. | |
| 5,453,517 A | 9/1995 | Kuhn et al. | |
| 5,459,276 A | 10/1995 | Kuhn et al. | |
| 5,501,980 A | 3/1996 | Katerinopolous et al. | |
| 5,516,911 A | 5/1996 | London et al. | |
| 5,773,227 A | 6/1998 | Kuhn et al. | |
| 6,057,114 A | 5/2000 | Akong et al. | |
| 6,162,931 A | 12/2000 | Gee et al. | |
| 6,420,183 B1 | 7/2002 | Krahn et al. | |
| 2001/0006820 A1 | 7/2001 | Knapp et al. | |
| 2002/0164616 A1 | 11/2002 | Martin et al. | |

OTHER PUBLICATIONS

Hodder et al. (2004) J. Biomol. Screen 9: 417-426.*
Adams, C.M.W., et al., "Permeability in Atherosclerosis," Atherosclerosis, 27, pp. 353-359 (1977).
Eidelman, O., and Cabantchik, Z. I., "Continuous Monitoring of Transport by Fluorescence on Cells and Vesicles," Biochim. Biophys. Acta, 988, pp. 319-334 (1989).
Molecular Probes Inc., Handbook of Fluorescent Probes and Research Chemicals, 7th edition, Chapter 1, Eugene, Oregon (1996-2007).
Davis, H.W., and Sauter, R.W., "Fluorescence of Trypan Blue in Frozen-Dried Embryos of the Rat," Histochemistry, 54, pp. 177-189 (1977).
Hathaway, W., et al., "The Acridine Orange Viability Test Applied to Bone Marrow Cells I. Correlation with Trypan Blue and Eosin Dye . . . ," Blook, 23, pp. 517-525 (2007).
Bacci, J., et al., "Efficient Two-Step Synthesis of 9-Aryl-6-hydroxy-3H-xanthen-3-one Fluorophores," Org. Chem., 70, pp. 9051-9053 (2005).
Lakowicz, J. R., "Topics in Fluorescence Spectroscopy," vol. 4: Probe Design and Chemical Sensing; Plenum Press, New York & London (1994).
Gee, K., et al., "Detection and Imaging of Zinc Secretion from Pancreatic B-Cells Using a New Fluorescent Zinc Indicator," J. Am. Chem. Soc., 124, pp. 776-778 (2002).
Martin, V., et al., "Fluorescent Sodium Ion Indicators Based on the 1, 7-diaza-15-crown-5 system," Bioorg. Med. Chem. Lett., 14, pp. 5313-5316 (2004).
Parham, W. E., and Bradscher, C. K., "Aromatic Organolithium Reagents Bearing Electrophilic Groups. Preparation by Halogen . . . ," Acc. Chem. Res., 15, pp. 300-305 (1982).
Chun et al., "D1-D2 Dopamine Receptor Synergy Promotes Calcium Signaling via Multiple Mechanisms", Molecular Pharmacology, vol. 84, pp. 190-200, (2013).
"Human CRAC (STIM1/ORAI1) Ion Channel Cell Line", Technical Data Sheet, PhotoScreen Ion Channel Cell Line, PerkinElmer, Inc., pp. 1-9, (2009).
Kurogi et al., "Green Tea Polyphenol Epigallocatechin Gallate Activates TRPA1 in an Intestinal Enteroendocrine Cell Line, STC-1", Chem. Senses, vol. 37, pp. 167-177, (2012).
Podust et al., "Extension of in vivo half-life of biologically active peptides via chemical conjugation to XTEN protein polymer", Protein Engineering, Design & Selection, vol. 26, No. 11, pp. 743-753, (2013).
Senbagavalli et al., "Immune Complexes Isolated from Patients with Pulmonary Tuberculosis Modulate the Activation and Function of Normal Granulocytes", Clinical and Vaccine Immunology, vol. 19, No. 12, pp. 1965-1971, (2012).

(Continued)

*Primary Examiner* — Michael Pak
(74) *Attorney, Agent, or Firm* — Bret E. Field; Glenn J. Foulds; Bozicevic, Field & Francis LLP

(57) ABSTRACT

Fluorescent dyes useful for preparing fluorescent metal ion indicators, the fluorescent indicators themselves, and the use of the fluorescent indicators for the detection, discrimination and quantification of metal cations.

18 Claims, 6 Drawing Sheets

(56) References Cited

OTHER PUBLICATIONS

Vicini, Rino, "Study of calcium signaling by fluorescent imaging", Studienwoche Schweizer Jugend forscht, Universite De Geneve, (2011).

Online "http://www.interchim.fr/cat/CalciumAssays.pdf Mar 31, 2004—Fluo-8 AM." "[PDF] Calcium Assays—Interchim" accessed Sep. 16, 2013.

Online: "http://www.teflabs.com/Portals/44052/docs/Fluo-2-MA-Info-Packet1.pdf" accessed Sep. 17, 2013.

* cited by examiner

FLUORESCEIN LACTONE ION INDICATORS AND THEIR APPLICATIONS

CROSS-REFERENCE TO RELATED APPLICATIONS

This application is a continuation-in-part of U.S. patent application Ser. No. 12/932,683, filed Mar. 2, 2011, which is a divisional of U.S. patent application Ser. No. 12/040,753, filed Feb. 29, 2008, which claims priority under 35 U.S.C. §119(e) to U.S. provisional patent application Ser. No. 60/923,452, filed Apr. 13, 2007, each of which is hereby incorporated by reference.

BACKGROUND

Metal ions play important roles in many biological systems. Cells utilize metal ions for a wide variety of functions, such as regulating enzyme activities, protein structures, cellular signaling, as catalysts, as templates for polymer formation and as regulatory elements for gene transcription. Metal ions can also have a deleterious effect when present in excess of bodily requirements or capacity to excrete. A large number of natural and synthetic materials are known to selectively or non-selectively bind to or chelate metal ions. Ion chelators are commonly used in solution for in vivo control of ionic concentrations and detoxification of excess metals, and as in vitro buffers. Ion chelators can be used as optical indicators of ions when bound to a fluorophore, and may be useful in the analysis of cellular microenvironments or dynamic properties of proteins, membranes and nucleic acids. For example, $Ca^{2+}$ ions play an important role in many biological events, and so the determination of intracellular $Ca^{2+}$ is an important biological application.

Fluorescent indicators utilizing a polycarboxylate BAPTA chelator have been predominantly used for intracellular calcium detections (see U.S. Pat. No. 4,603,209; U.S. Pat. No. 5,049,673; U.S. Pat. No. 4,849,362; U.S. Pat. No. 5,453,517; U.S. Pat. No. 5,501,980; U.S. Pat. No. 5,459,276; U.S. Pat. No. 5,501,980; U.S. Pat. No. 5,459,276; and U.S. Pat. No. 5,516,911; each of which is hereby incorporated by reference). Xanthene-based fluorescent calcium indicators (such as Fluo-3, Fluo-4 and Rhod-) are the most common fluorescent indicators used in biological assays. However, these existing xanthene-based calcium indicators typically have low fluorescence quantum yields, resulting in low detection sensitivity. Furthermore their corresponding acetoxymethyl esters may not readily penetrate the membranes of live cells (thus requiring higher temperatures to achieve optimal dye loading), and once inside the cells, they exhibit a slow conversion to the corresponding BAPTA free acid.

In view of the existing drawbacks for currently used xanthene-based fluorescent calcium indicators, what is needed are improved compositions and methods that offer sensitive detection of small variations in calcium concentrations, with a rapid response and a strong fluorescence signal. Also needed are fluorescent indicators that can be readily loaded into live cells. In addition, compositions and methods that are less susceptible to the effects of external changes (such as temperature) are preferred for high throughput screening and high content analysis.

The present application is directed to a family of fluorescent metal ion dyes that are useful for preparing fluorescent metal ion indicators. The indicators include a fluorescein lactone fluorophore and an ionophore, and are useful for the detection, discrimination and quantification of metal cations. The fluorescent indicators of this invention demonstrate unexpected better cellular retention compared to the existing fluorescein ion indicators.

DEFINITIONS

Figure 1:
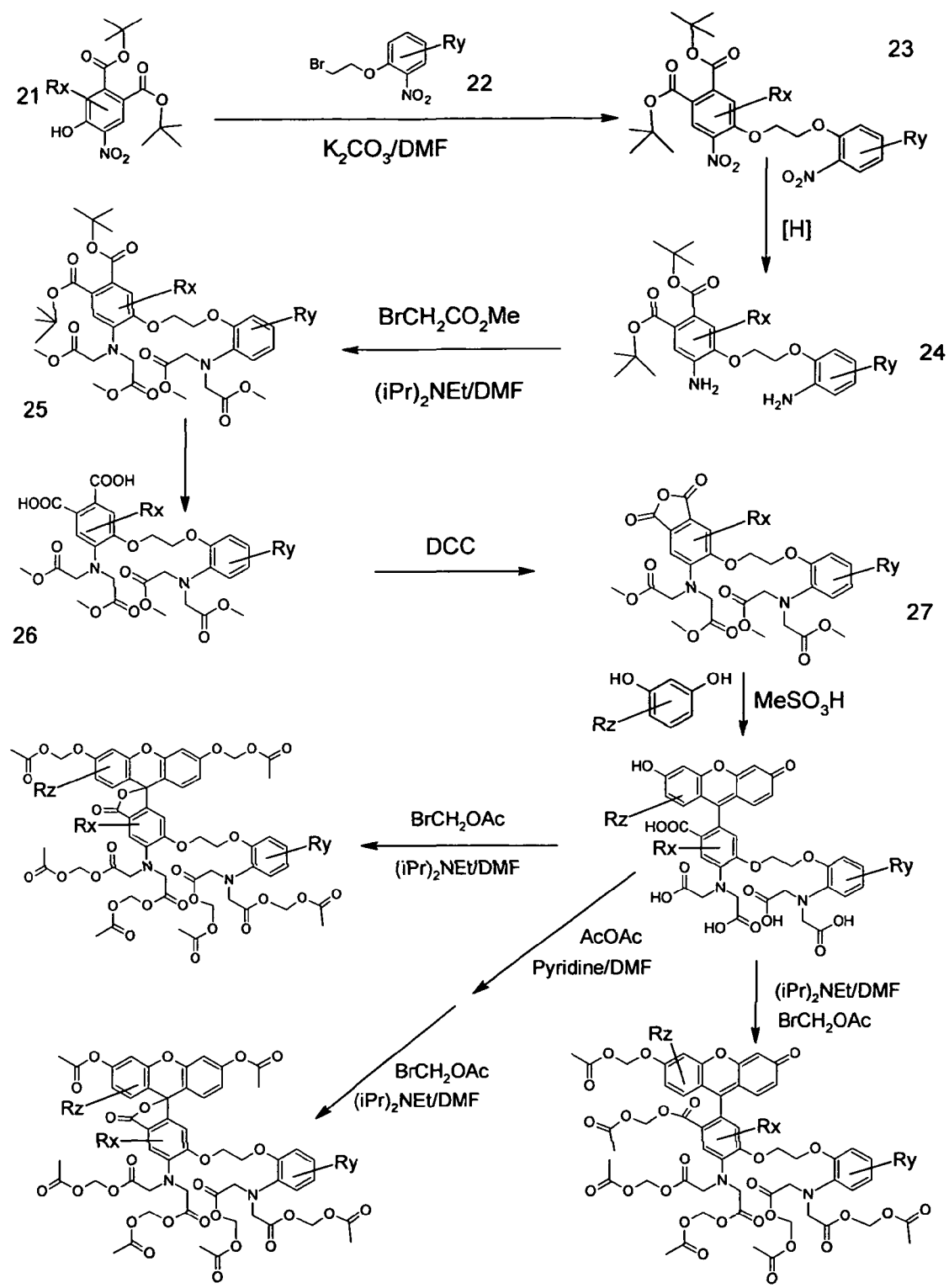
FIG. 1. A synthetic scheme for the preparation of BAPTA anhydride compounds and xanthene-substituted BAPTA compounds, where Rx, Ry and Rz represent one or more substituents of each ring.

The following definitions are set forth to illustrate and define the meaning and scope of the various terms used to describe the invention herein.

The term "organic substituent", as used herein, refers to a carbon-containing organic radical that incorporates straight, branched chain or cyclic radicals having up to 50 carbons, unless the chain length or ring size is limited thereto. The organic substituent may include one or more elements of unsaturation, such as carbon-carbon double or triple bonds. Organic substituents may include alkyl, alkylene, alkenyl, alkenylene and alkynyl moieties, among others.

The term "alkyl," as used herein, by itself or as part of another group, refers to straight, branched chain or cyclic radicals having up to 50 carbons, unless the chain length or ring size is limited thereto, such as methyl, ethyl, propyl, cyclopropanyl, isopropyl, butyl, t-butyl, isobutyl, pentyl, hexyl, cyclohexyl, isohexyl, heptyl, 4,4-dimethylpentyl, octyl, 2,2,4-trimethylpentyl, nonyl, and decyl, among others.

The term "alkylene," as employed herein, by itself or as part of another group, refers to straight, branched chain or cyclic divalent radicals having up to 50 carbons, unless the chain length or ring size is limited thereto. Typical examples include methylene ($—CH_2—$), ethylene ($—CH_2CH_2—$), propylene, butylene, pentylene, hexylene, heptylene, octylene, nonylene, and decylene, among others.

The term "alkenyl," as used herein, by itself or as part of another group, means a straight, branched chain or cyclic radical having 2-50 carbon atoms and one or more carbon-carbon double bonds, unless the chain length or ring size is limited thereto, such as ethenyl, 1-propenyl, 2-propenyl, 2-methyl-1-propenyl, 1-butenyl, and 2-butenyl, among others. The alkenyl chain may be 2 to 10 carbon atoms in length. Alternatively, the alkenyl chain may be 2 to 4 carbon atoms in length.

The term "alkenylene," as used herein, by itself or as part of another group, means straight, branched chain or cyclic divalent radical having 2-50 carbon atoms, unless the chain length or ring size is limited thereto, said straight, branched chain or cyclic radical containing at least one carbon-carbon double bond. Typical examples include ethenylene (—CH═CH—), propenylene (—CH═CHCH$_2$— and —CH$_2$CH═CH—), n-butenylene, and 3-methyl-2-pentenylene, hexenylene, heptenylene, octenylene, nonenylene, and decenylene, among others.

The term "alkynyl," as used herein, by itself or as part of another group, means a straight, branched chain or cyclic radical of 2-50 carbon atoms, unless the chain length or ring size is limited thereto, having at least one carbon-carbon triple bond between two of the carbon atoms in the chain, such as acetylenyl, 1-propynyl, and 2-propynyl, among others. The alkynyl chain may be 2 to 10 carbon atoms in length. Alternatively, the alkynyl chain may be from 2 to 4 carbon atoms in length.

The term "alkynylene" as used herein, by itself or as part of another group, means a straight, branched chain or cyclic divalent radical having 2-50 carbon atoms, unless the chain length or ring size is limited thereto, that contains at least one carbon-carbon triple bond. Typical examples include ethynylene (—C≡C—), propynylene (—C≡CCH$_2$— and —CH$_2$C≡C—), n-butynylene, 4-methyl-2-pentynylene, 1-butynylene, 2-butynylene, 3-butynylene, 4-butynylene, pentynylene, hexynylene, heptynylene, octynylene, nonynylene, and decynylene, among others.

The term "alkoxy" as used herein, by itself or as part of another group, refers to any of the above radicals linked via an oxygen atom. Typical examples include methoxy, ethoxy, isopropyloxy, sec-butyloxy, n-butyloxy, t-butyloxy, n-pentyloxy, 2-methylbutyloxy, 3-methylbutyloxy, n-hexyloxy, and 2-ethylbutyloxy, among others. Alkoxy also may include PEG groups (—OCH$_2$CH$_2$O—) or alkyl moieties that contain more than one oxygen atom.

The term "aryl," as employed herein, by itself or as part of another group, refers to an aryl or aromatic ring system containing 1 to 4 unsaturated rings (each ring containing 6 conjugated carbon atoms and no heteroatoms) that are optionally fused to each other or bonded to each other by carbon-carbon single bonds, that is optionally further substituted as described below. Examples of aryl ring systems include, but are not limited to, substituted or unsubstituted derivatives of phenyl, biphenyl, o-, m-, or p-terphenyl, 1-naphthyl, 2-naphthyl, 1-, 2-, or 9-anthryl, 1-, 2-, 3-, 4-, or 9-phenanthrenyl and 1-, 2- or 4-pyrenyl. Aryl substituents may include phenyl, substituted phenyl, naphthyl or substituted naphthyl.

The term "heteroaryl," as employed herein, by itself or as part of another group, refers to groups having 5 to 14 ring atoms; 6, 10 or 14 π electrons shared in a cyclic array; and containing carbon atoms and 1, 2, 3, or 4 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, carbazolyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups).

Any aryl or heteroaryl ring system is unsubstituted or optionally and independently substituted by any synthetically accessible and chemically stable combination of substituents, such as H, halogen, cyano, sulfo, alkali or ammonium salt of sulfo, nitro, carboxy, alkyl, perfluoroalkyl, alkoxy, alkylthio, amino, monoalkylamino, dialkylamino or alkylamido, the alkyl portions of which having 18 or fewer carbons.

The terms "halogen" or "halo" as employed herein, by itself or as part of another group, refers to chlorine, bromine, fluorine or iodine.

The terms "AM ester" or "AM" as employed herein, by itself or as part of another group, refers to an acetoxymethyl ester of a carboxylic acid or a phenol.

The terms "amino" or "amine" include NH$_2$, "monoalkylamine" or "monoalkylamino," and "dialkylamine" or "dialkylamino". The terms "monoalkylamine" and "monoalkylamino," "dialkylamine" and "dialkylamino as employed herein, by itself or as part of another group, refers to the group NH$_2$ where one hydrogen has been replaced by an alkyl group, as defined above.

The terms "dialkylamine" and "dialkylamino" as employed herein, by itself or as part of another group, refers to the group NH$_2$ where both hydrogens have been replaced by alkyl groups, as defined above.

The term "hydroxyalkyl," as employed herein, by itself or as part of another group, refers to an alkyl group where one or more hydrogens thereof are substituted by one or more hydroxyl moieties.

The term "haloalkyl," as employed herein, by itself or as part of another group, refers to an alkyl group where one or more hydrogens thereof are substituted by one or more halo moieties. Typical examples include chloromethyl, fluoromethyl, difluoromethyl, trifluoromethyl, trichloroethyl, trifluoroethyl, fluoropropyl, and bromobutyl, among others.

The term "haloalkenyl," as employed herein, by itself or as part of another group, refers to an alkenyl group where one or more hydrogens thereof are substituted by one or more halo moieties.

The term "haloalkynyl," as employed herein, by itself or as part of another group, refers to an alkynyl group where one or more hydrogens thereof are substituted by one or more halo moieties.

The term "carboxyalkyl," as employed herein, by itself or as part of another group, refers to an alkyl group where one or more hydrogens thereof are substituted by one or more carboxylic acid moieties.

The term "heteroatom" as used herein, by itself or as part of another group, means an oxygen atom ("O"), a sulfur atom ("S") or a nitrogen atom ("N"). It will be recognized that when the heteroatom is nitrogen, it may form an NR$_1$R$_2$ moiety, where R$_1$ and R$_2$ are, independently from one another, hydrogen or alkyl, or together with the nitrogen to which they are bound, form a saturated or unsaturated 5-, 6-, or 7-membered ring.

The term "chelator", "chelate", "chelating group", "ionophore", or "ionophoric moiety" as used herein, by itself or as part of another group, refers to a chemical moiety that binds to, or complexes with, one or more metal ions, such as lithium, calcium, sodium, magnesium, potassium, and/or other biologically important metal ions. The binding affinity of a chelator for a particular metal ion can be determined by measuring the dissociation constant between that chelator and that ion. Chelators may include one or more chemical moieties that bind to, or complex with, a cation or anion. Examples of suitable chelators include 1,2-bis(2-aminophenoxy)ethane-N,N,N',N'-tetraacetic acid (BAPTA), bipyridyl (bipy); terpyridyl (terpy); ethylenediaminetetraacetic acid (EDTA); crown ethers; aza-crown ethers; succinic acid; citric acid; salicylic acids; histidines; imidazoles; ethyleneglycol-bis-(beta-aminoethyl ether) N,N'-tetraacetic acid (EGTA); nitroloacetic acid; acetylacetonate (acac); sulfate; dithiocarbamates; carboxylates; alkyldiamines; ethylenediamine (en); diethylenetriamine (dien); nitrate; nitro; nitroso; glyme; diglyme; bis(acetylacetonate)ethylenediamine (acacen); 1,4,7,10-tetraazacyclododecanetetraacetic acid (DOTA), 1,4,7,10-tetraazacyclododecane-1,4,7-triacetic acid (DO3A), 1-oxa-4,7,10-triazacyclododecane-triacetic acid (OTTA), 1,4,7-triazacyclononanetriacetic acid (NOTA), 1,4,8,11-tetraazacyclotetra-decanetetraacetic acid (TETA), DOTA-N-(2-aminoethyl)amide; DOTA-N-(2-aminophenethyl)amide; and 1,4,8,11-tetraazacyclotetradecane, among others.

The term "BAPTA" or "1,2-bis(2-aminophenoxy)ethane-N,N,N',N'-tetraacetic acid" as used herein, by itself or as part of another group, refers to the following ring structure or its derivatives, such as esters, amides, carbamates and so on:

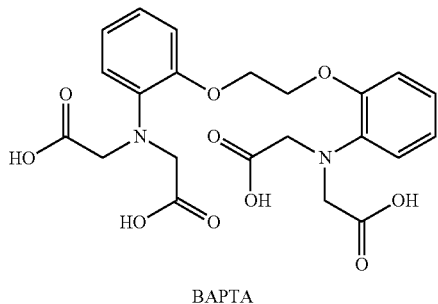

BAPTA

The term "fluorophore or fluorophore moiety" as used herein, by itself or as part of another group, means a molecule or a portion of a molecule which exhibits fluorescence. By fluorescence is meant that the molecule or portion of a molecule can absorb excitation energy having a given wavelength and emit energy at a different wavelength. The intensity and wavelength of the emitted energy depend on the fluorophore, the chemical environment of the fluorophore, and the specific excitation energy used. Exemplary fluorophores include, but are not limited to, fluoresceins, rhodamines, coumarins, oxazines, cyanines, pyrenes, and other polycyclic aromatic molecules.

The term "xanthene", or "xanthene derivative", as used herein, by itself or as part of another group, means any compounds or substituents that contain one or more of the following fused ring structures or its derivatives:

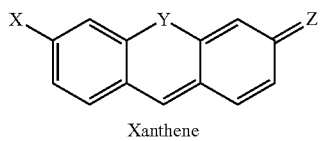

Xanthene
(X, Z = O, S or Se or N; Y = O, S, Se, N, C, or Si)

The term "fluorescein" as used herein, by itself or as part of another group, means any compounds or substituents that contain one or more of the following fused ring structures or its derivatives:

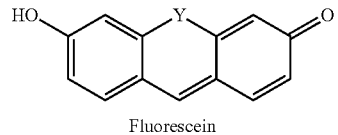

Fluorescein
(Y = O, S, Se, N, C or Si)

The term "fluorescein lactone" as used herein, by itself or as part of another group, means any compounds or substituents that contain one or more of the following fused ring structures or its derivatives:

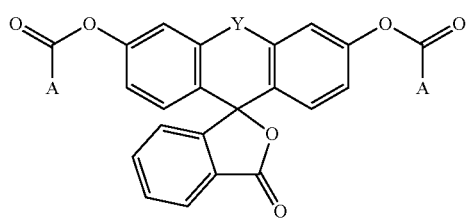

Fluorescein Lactone
(Y = O, S, Se, N, C or Si)

The term "substituted," as used herein, refers to the formal replacement of a hydrogen on a chemical moiety or functional group with an alternative radical. Where a compound, chemical moiety or functional group is described as substituted, the alternative radical substituent moiety is generally selected from the group consisting of hydroxy, oxo, nitro, trifluoromethyl, halogen, alkoxy, alkylenedioxy, aminoalkyl, aminoalkoxy, amino, monoalkylamino, dialkylamino, alkylcarbonylamino, alkoxycarbonylamino, alkoxycarbonyl, carboxy, hydroxyalkoxy, alkoxyalkoxy, monoalkylaminoalkoxy, dialkylaminoalkoxymono(carboxyalkyl)amino, bis(carboxy-alkyl)amino, alkoxycarbonyl, alkynylcarbonyl, alkylsulfonyl, alkenylsulfonyl, alkynylsulfonyl, arylsulfonyl, alkylsulfinyl, alkylsulfonamido, arylsulfonamido, carboxyalkoxy, carboxyalkyl, carboxyalkylamino, cyano, trifluoromethoxy, perfluoroethoxy, guanidine, amidino, oxyguanidino, alkylimino, formylimino, acyl nitrile, acyl azide, acetyl azide, dichlorotriazene, isothiocyante, sulfonyl halide, sulfosuccinimidyl ester, isocyante, acyl halide, aldehyde, haloacetamide, maleimido, aziridinyl, alkylthio (disulfide), acrylo, haloalkylcarbonyl, boronate, hydrazide, semicarbazide, carbohydrazide, arylalkyl, heteroarylalkyl, cycloalkylalkyl, cycloalkenylalkyl, cycloheteroalkylalkyl, and cycloheteroalkenylalkyl.

The term "indicator compound" refers to the compounds of the invention, specifically to those compounds having utility as fluorescent metal ion indicators, as well as their acylated or otherwise protected precursor compounds, such as the acetoxymethyl ester derivatives suitable for adding to samples containing biological cells.

The term "screening" refers to the testing and/or evaluation of a multiplicity of molecules or compounds for a selected property or therapeutic utility. Screening is typically a repetitive, or iterative process. A multiplicity of candidate molecules may be screened for their ability to bind to a target molecule which is capable of denaturing and/or unfolding. For example, a multiplicity of candidate molecules may be evaluated for their ability to bind to a target molecule (e.g., a protein receptor) in a thermal shift assay. If none of a selected subset of molecules from the multiplicity of candidate molecules (for example, a combinatorial library) binds to the target molecule, then a different subset may be tested for binding in the thermal shift assay.

The term "high-throughput", as used herein, encompasses screening activity in which human intervention is minimized, and automation is maximized. For example, high-throughput screening may include any of a variety of automated processes, including for example the automation of pipetting, mixing, and/or heating, the software-controlled generation of thermal unfolding information, and the software-controlled comparisons of thermal unfolding information. Alternatively, a high-throughput method is one in which hundreds of compounds can be screened per 24 hour period by a single individual operating a single suitable apparatus.

DESCRIPTION OF THE PREFERRED EMBODIMENTS

The present application is directed to fluorescent dyes useful for preparing fluorescent metal ion indicators, the fluorescent indicators themselves, and the use of the fluorescent indicators for the detection, discrimination and quantification of metal cations.

In one aspect of the invention, the compounds of the invention may be described by Formula 1:

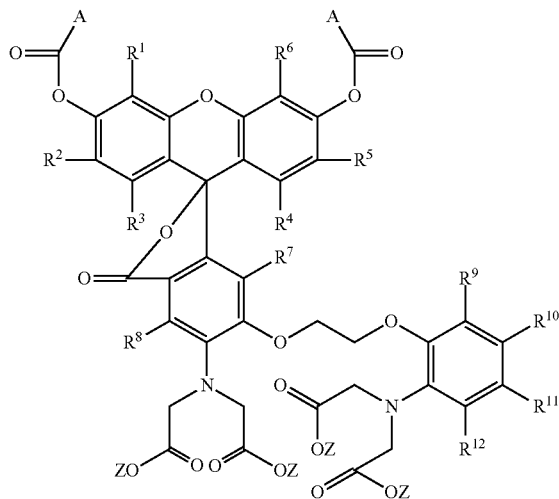

Formula 1

In this embodiment, substituents $R^1$-$R^{12}$ are independently H, halogen, carboxy, alkoxy, aryloxy, thiol, allylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl. A is an alkyl having 1-10 carbons. Preferably A is methyl. Z is an acyloxymethyl having 1-10 carbons. Preferably Z is acetoxymethyl.

In yet another aspect of the invention, the compounds of the invention may be described by Formula 2:

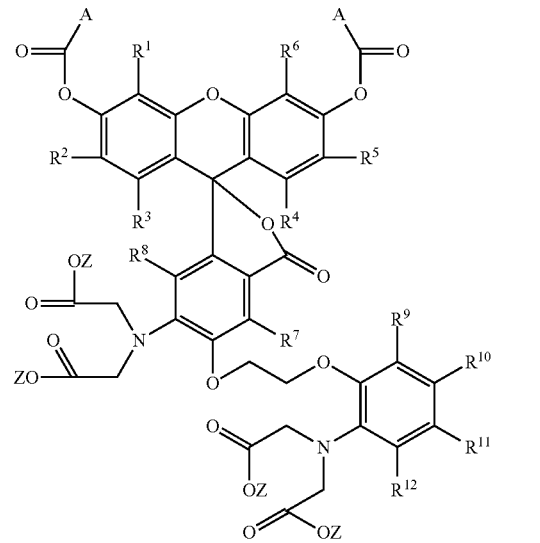

Formula 2

In this embodiment, substituents $R^1$-$R^{12}$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl. A is an alkyl having 1-10 carbons. Preferably A is methyl. Z is an acyloxymethyl having 1-10 carbons. Preferably Z is acetoxymethyl.

In yet another aspect of the invention, the compounds of the invention are fluorescent indicators which can be described by Formula 3.

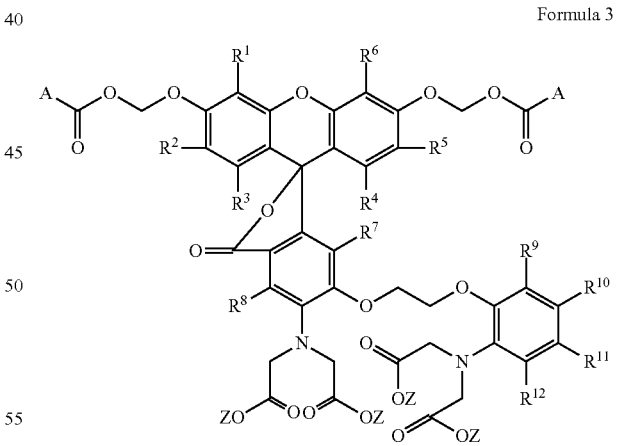

Formula 3

In this embodiment, substituents $R^1$-$R^{12}$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl. A is an alkyl having 1-10 carbons. Preferably A is methyl. Z is an acyloxymethyl having 1-10 carbons. Preferably Z is acetoxymethyl.

In yet another aspect of the invention, the compounds of the invention are fluorescent indicators which can be described by Formula 4.

Formula 4

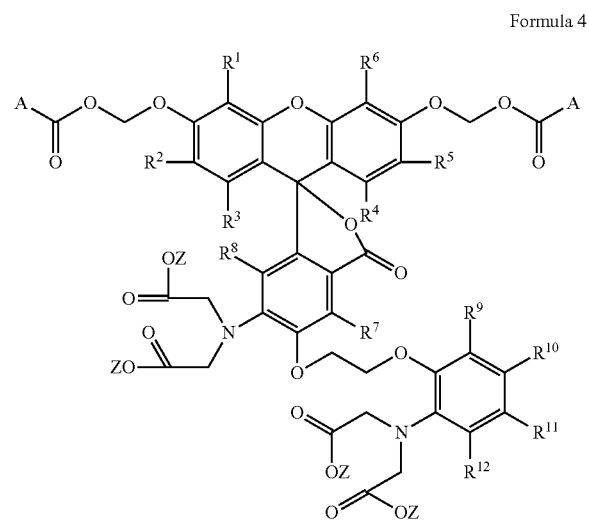

In this embodiment, substituents $R^1$-$R^{12}$ are independently H, halogen, carboxy, alkoxy, aryloxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl. A is an alkyl having 1-10 carbons. Preferably A is methyl. Z is an acyloxymethyl having 1-10 carbons. Preferably Z is acetoxymethyl.

The fluorophore moiety can be any compound described by any of Formulas 1-4 that exhibits an absorption maximum beyond 450 nm, that is bound to a chelator by a covalent linkage L, or that is fused to a chelator. The covalent linkage L may be a single covalent bond, or a suitable combination of stable chemical bonds, as described in greater detail below. The covalent linkage binding the fluorophore moiety to the chelator is typically a single bond, but optionally incorporates 1-20 nonhydrogen atoms selected from the group consisting of C, N, O, P, and S.

As described above, where the fluorophore moiety is a xanthene, the resulting compound may be a fluorescein, a rhodol (U.S. Pat. No. 5,227,487, hereby incorporated by reference), or a rhodamine. As used herein, fluorescein includes benzo- or dibenzofluoresceins, seminaphthofluoresceins, or naphthofluoresceins. Similarly, as used herein rhodol includes seminaphthorhodafluors (U.S. Pat. No. 4,945,171, hereby incorporated by reference). Fluorinated xanthene dyes have been described previously as possessing particularly useful fluorescence properties (U.S. Pat. No. 6,162,931, hereby incorporated by reference).

In one aspect of the invention, the fluorophore moiety has an absorption maximum beyond 480 nm. In a particularly useful embodiment, the fluorophore moiety absorbs at or near 488 nm to 514 nm, and so is particularly suitable for excitation by the output of an argon-ion laser excitation source, or near 546 nm, and so is particularly suitable for excitation by a mercury arc lamp.

The fluorophore moiety is typically selected to confer its fluorescence properties on the indicator compound it is incorporated into. That is, the resulting indicator compound exhibits a detectable optical response when excited by energy having a wavelength at which that fluorophore absorbs as used herein, a detectable optical response means a change in, or occurrence of, an optical property that is detectable either by observation or instrumentally, such a change in absorption (excitation) wavelength, fluorescence emission wavelength, fluorescence emission intensity, fluorescence polarization, or fluorescence lifetime, among others.

In addition, the compounds of the invention preferably exhibit a detectable change in the optical response upon binding a target metal ion. Where the detectable response is a fluorescence response, the detectable change is typically a change in fluorescence, such as a change in the intensity, excitation or emission wavelength distribution of fluorescence, fluorescence lifetime, fluorescence polarization, or a combination thereof. Preferably, the change in optical response upon binding the target metal ion is a change in fluorescence intensity that is greater than approximately 50-fold, more preferably greater than 100-fold.

Synthesis

The compounds of the invention may be prepared using any suitable synthetic scheme. The methodology used to prepare the compounds of the invention may involve two components. The first component may involve the formation of the chelator, while the second may involve the modification of the chelator by forming a reactive functional group, covalently attaching a conjugate, or covalently attaching a fluorophore moiety to form the desired indicator compound. Although these synthetic components are typically performed in the order given, they may be carried out in any other suitable sequence. For example, a portion of the chelator may be derivatized with a fluorescent dye prior to formation of the complete chelator ring. The representative synthetic methods are summarized in FIG. 1. The appropriate methods may be used to synthesize the desired compounds of the invention.

As the metal binding ability of the resulting chelators may be significantly influenced by the nature of the amine substituents, careful selection of the alkylating agent may be necessary to prepare a reporter for a particular target ion. BAPTA chelators are typically selective for calcium ion. Where the chelator nitrogens are alkylated by methyl bromoacetate, the resulting bis-aza-crown ether is typically selective for sodium ions. If the alkylating agent is 2-picolyl chloride, the resulting crown ether is typically selective for zinc ions. Selection of an alkylating agent that incorporates a precursor to a reactive functional group is useful for producing chemically reactive compounds of the invention, as well as acting as a useful intermediate for preparing conjugates, as described above.

The syntheses of chelating groups selective for different metal ions has been well described in the literature (U.S. Pat. No. 4,603,209; U.S. Pat. No. 5,049,673; U.S. Pat. No. 4,849,362; U.S. Pat. No. 5,453,517; U.S. Pat. No. 5,501,980; U.S. Pat. No. 5,459,276; U.S. Pat. No. 5,501,980; U.S. Pat. No. 5,459,276; U.S. Pat. No. 5,516,911; U.S. Application No. 2002/0164616; each of which is incorporated by reference). These methods can be readily adapted to prepare chelator intermediates useful for the synthesis of the compounds of the invention.

Synthesis of conventional xanthene dyes such as fluoresceins, rhodamines and rhodols typically involves the condensation of two equivalents of resorcinol (for fluoresceins), aminophenol (for rhodamines) or a mixture of a resorcinol and an aminophenol (for rhodols) with a carbonyl-containing moiety such as a phthalic acid derivative or benzaldehyde derivatives. However, in the synthesis of the xanthene indicators of the invention, the desired resorcinol or aminophenol is condensed with a chelator intermediate that contains a carboxylic acid, anhydride or acyl halide bound directly to the chelating moiety. This synthetic method is illustrated in FIG. 1.

Alternatively the fluorescent indicators of the invention can be prepared via the condensation of properly protected xanthones with a chelator anion, typically prepared from the corresponding chelator bromide or iodide. This organometallic chemistry is also well described in the literature (C. Chen, R. Yeh and D. S. Lawrence, J. Am. Chem. Soc. 2002, 124, 3840; U.S. Pat. No. 5,049,673); Y. Urano, M. Kamiya, K. Kanda, T. Ueno, K. Hirose and T. Nagano, J. Am. Chem. Soc. 2005, 127, 4888; each of which is incorporated by reference) and can be readily adapted to synthesize the compounds of the invention.

Post-condensation modifications of both the chelator and the fluorophore moiety are typically analogous to known methods of indicator modification. For example, the reduction of nitro substituents to amino groups, the conversion of carboxy substituents to cyano groups, and the preparation of esters of carboxylic acids, including acetoxymethyl esters. Additionally, a given salt or counterion of the indicators of the invention may be readily converted to other salts by treatment with ion-exchange resins, selective precipitation, and basification, as is well-known in the art.

Post-condensation modifications of xanthylium dyes are well known. For instance, the xanthenone portion of the dye can be halogenated by treatment with an appropriate halogenating agent, such as liquid bromine. Xanthenes containing unsaturated fused rings can be hydrogenated to the saturated derivatives.

The reduced and oxidized versions of the xanthene indicators are freely interconvertible by well-known oxidation or reduction reagents, including borohydrides, aluminum hydrides, hydrogen/catalyst, and dithionites. Care must be exercised to select an oxidation or reducing agent that is compatible with the chelator used. A variety of oxidizing agents mediate the oxidation of dihydroxanthenes, including molecular oxygen in the presence or absence of a catalyst, nitric oxide, peroxynitrite, dichromate, triphenylcarbenium and chloranil. The dihydroxanthenes may also be oxidized electrochemically, or by enzyme action, including the use of horseradish peroxidase in combination with peroxides or by nitric oxide.

Applications of the Fluorescent Indicators of the Invention

The indicators disclosed herein possess particular utility for the detection and/or quantification of metal ions in a sample of interest. Such indicators may be useful for measuring ions in extracellular spaces; in vesicles; in vascular tissue of plants and animals; biological fluids such as blood and urine; in fermentation media; in environmental samples such as water, soil, waste water and seawater; and in chemical reactors. Optical indicators for ions are important for qualitative and quantitative determination of ions, particularly in living cells. Fluorescent indicators for metal cations also permit the continuous or intermittent optical determination of these ions in living cells, and in solutions containing the ions.

In effecting such determination, the substance to be determined, or analyte, which contains the ion of interest is contacted with a fluorescent indicator as disclosed above. Complexation of the metal ion in the chelator of the indicator results in a detectable change in the fluorescence properties of the indicator. Detection and optionally quantification of the detectable change permits the ion of interest to be detected and optionally quantified.

Upon binding the target ion in the chelating moiety of the indicator, the optical properties of the attached fluorophore are generally affected in a detectable way, and this change may be correlated with the presence of the ion according to a defined standard. Compounds having relatively long wavelength excitation and emission bands can be used with a variety of optical devices and require no specialized (quartz) optics, such as are required by indicators that are excited or that emit at shorter wavelengths. These indicators are suitable for use in fluorescence microscopy, flow cytometry, fluorescence microplate readers, or any other application that currently utilize fluorescent metal ion indicators.

This determination method may be based on the so-called "PET effect", or the transfer, induced by photons, of electrons (photoinduced electron transfer=PET) from the ionophoric moiety or ionophore, respectively, to the fluorophore moiety or fluorophore, respectively, which leads to a decrease in the (relative) fluorescence intensity and the fluorescence decay time of the fluorophore. Absorption and emission wavelengths, however, are not significantly affected in the process (J. R. Lakowicz in "Topics in Fluorescence Spectroscopy", Volume 4: Probe Design and Chemical Sensing; Plenum Press, New York & London (1994)).

By the binding of ions to the ionophore, the PET effect may be partly or completely inhibited, so that there is an increase in the fluorescence of the fluorophore moiety. Hence, the concentration or the activity of the ion to be determined can be deduced by measuring the change in fluorescence properties, i.e. fluorescence intensity and/or fluorescence decay time.

A variety of fluorescent indicators that are useful for the detection of biologically relevant soluble free metal ions (such as $Ca^{2+}$, $Mg^{2+}$ and $Zn^{2+}$) have been described that utilize oxygen-containing anionic or polyanionic chelators to bind to metal ions. In general, a useful property for metal ion indicators is selectivity, or the ability to detect and/or quantify a selected metal ion in the presence of other metal ions. Discrimination of $Ca^{2+}$, $Na^+$ and $K^+$ ions in the presence of other metal ions is particularly advantageous in certain biological or environmental samples. For most biological applications, it is useful that the indicators be effective in aqueous solutions. It is also beneficial if the indicator absorbs and emits light in the visible spectrum where biological materials typically have low intrinsic absorbance or fluorescence.

Optical methods using fluorescence detection of metal ions permit measurement of the entire course of ion flux in a single cell as well as in groups of cells. The advantages of monitoring transport by fluorescence techniques include the high level of sensitivity of these methods, temporal resolution, modest demand for biological material, lack of radioactivity, and the ability to continuously monitor ion transport to obtain kinetic information (Eidelman, O. Cabantchik, Z. I. Biochim. Biophys. Acta, 1989, 988, 319-334). The general principle of monitoring transport by fluorescence is based on having compartment-dependent variations in fluorescence properties associated with translocation of compounds.

Optical methods were developed initially for measuring $Ca^{2+}$ ion flux (U.S. Pat. No. 5,049,673, hereby incorporated by reference; Scarpa, A. Methods of Enzymology, 1979, 56, 301 Academic Press, Orlando, Fla.; Tsien, R. Y. Biochemistry, 1980, 19, 2396; Grynkiewicz, G., Poenic, M., Tsien, R. Y. J. Biol. Chem., 260, 3440) and have been modified for high-throughput assays (U.S. Pat. No. 6,057,114, hereby incorporated by reference). The flux of $Ca^{2+}$ ion is typically performed using calcium-sensitive fluorescent dyes such as Fluo-3, Fluo-4, Calcium Green, and others.

In particular, fluorescent indicators utilizing a polycarboxylate BAPTA chelator have been previously described. A determination method utilizing aza-cryptands as the chelator moiety and using xanthenes and coumarins as fluorophores has also been described (U.S. Pat. No. 5,439,828 and US Patent Application 20020164616; each hereby incorporated by reference). These aza-cryptand may, depending on their structure, exhibit selectivity for lithium, sodium or potassium ions. Some fluorescent indicators selective for $Li^+$, $Na^+$ and $K^+$ in aqueous or organic solution have also been described, based on the chemical modification of crown ethers (U.S. Pat. No. 5,134,232; U.S. Pat. No. 5,405,975, each hereby incorporated by reference).
ion.

The desired indicator compound is generally prepared for use as a detection reagent by dissolving the indicator in solution at a concentration that is optimal for detection of the indicator at the expected concentration of the target ion. Modifications that are designed to enhance permeability of the indicator through the membranes of live cells, such as functionalization of carboxylic acid moieties using acetoxymethyl esters and acetates, may require the indicator to be predissolved in an organic solvent such as dimethylsulfoxide (DMSO) before addition to a cell suspension, where the indicators may then readily enter the cells. Intracellular enzymes then cleave the esters, generating more polar acids and phenols which are then well-retained inside the cells. For applications where permeability of cell-membranes is required, the indicators of the invention are typically substituted by only one fluorophore.

The specific indicator used in a particular assay or experiment may be selected based on the desired affinity for the target ion as determined by the expected concentration range in the sample, the desired spectral properties, and the desired selectivity. Initially, the suitability of a material as an indicator of ion concentration is commonly tested by mixing a constant amount of the indicating reagent with a measured amount of the target ion under the expected experimental conditions.

Where the binding of an ion in the metal ion-binding moiety of the indicator results in a detectable change in spectral properties of the indicator compound, that indicator may be used for the detection and/or quantification of that ion (the target ion). Although the change in spectral properties may include for example a change in absorption intensity or wavelength, preferably the change in spectral properties is a detectable fluorescence response. Preferred indicators display a high selectivity, that is, they show a sufficient rejection of non-target ions. The interference of a non-target ion is tested by a comparable titration of the indicator with that ion. In one aspect of the invention, the target ions for the indicators of the present invention are selected from $Ca^{2+}$, $Na^+$ and $K^+$.

A detectable fluorescence response, as used herein, is a change in a fluorescence property of the indicator that is capable of being perceived, either by direct visual observation or instrumentally, the presence or magnitude of which is a function of the presence and/or concentration of a target metal ion in the test sample. This change in a fluorescence property is typically a change in fluorescence quantum yield, fluorescence polarization, fluorescence lifetime, a shift in excitation or emission wavelength, among others, or a combination of one or more of such changes in fluorescence properties. The detectable change in a given spectral property is generally an increase or a decrease. However, spectral changes that result in an enhancement of fluorescence intensity and/or a shift in the wavelength of fluorescence emission or excitation may also be useful. The change in fluorescence on ion binding may be due to conformational or electronic changes in the indicator that may occur in either the excited or ground state of the fluorophore, due to changes in electron density at the ion binding site, due to quenching of fluorescence by the bound target metal ion, or due to any combination of these or other effects.

A typical indicator for a specific target ion is an indicator that exhibits at least a 50-fold change in net fluorescence emission intensity (either an increase or decrease), or at least a 1 nanosecond difference in fluorescence lifetime (either shorter or longer). In one aspect of the invention, the indicator exhibits a 50-fold or greater change in net fluorescence emission intensity, and/or a 100% change in fluorescence lifetime in the presence of the target ion. In an alternative aspect of the invention, the indicator exhibits a shift in excitation or emission wavelength of at least 10 nm (either to shorter or longer wavelength), more preferably exhibiting a wavelength shift of 25 nm or greater.

The spectral response of a selected indicator to a specific metal ion is a function of the characteristics of the indicator in the presence and absence of the target ion. For example, binding to a metal ion may alter the relative electron densities of the fluorophore and the metal binding site. Additionally, or in the alternative, some metal ions may quench fluorescence emission when in close proximity to a fluorophore (heavy atom quenching). In one embodiment of the invention, the indicator is essentially nonfluorescent or exhibits low fluorescence in target ion-free solution and exhibits an increase in fluorescence intensity or fluorescence lifetime (or both) upon target metal ion binding.

As the optical response of the indicating reagent is typically determined by changes in fluorescence, the threshold of detection of the target ion will be dependent upon the sensitivity of the equipment used for its detection.

If the optical response of the indicator will be determined using fluorescence measurements, the sample of interest is typically stained with indicator concentrations of $10^{-9}$ M to $10^{-3}$ M. The most useful range of analyte concentration includes about one log unit above and below the dissociation constant of the ion-indicator complex. This dissociation constant may be determined by titration of the indicator with known concentrations of the target ion, usually over the range of virtually zero concentration to approximately 100 mM of the target ion, depending on which ion is to be measured and which indicator is being used. The dissociation constant may be affected by the presence of other ions, particularly ions that have similar ionic radii and charge. It may also be affected by other conditions such as ionic strength, pH, temperature, viscosity, presence of organic solvents and incorporation of the sensor in a membrane or polymeric matrix, or conjugation or binding of the sensor to a protein or other biological molecule. Any or all of these effects are readily determined, and can be taken into account when calibrating a selected indicator.

The indicator is typically combined with a sample in a way that will facilitate detection of the target ion concentration in the sample. The sample is generally a fluid or liquid suspension that is known or suspected to contain the target ion.

Representative samples include intracellular fluids from cells such as in blood cells, cultured cells, muscle tissue, neurons and the like; extracellular fluids in areas immediately outside of cells; fluids in vesicles; fluids in vascular tissue of plants and animals; biological fluids such as blood, saliva, and urine; biological fermentation media; environmental samples such as water, soil, waste water and sea water; industrial samples such as pharmaceuticals, foodstuffs and beverages; and samples from chemical reactors. Detection and quantitation of the target ion in a sample can help characterize the identity of an unknown sample, or facilitate quality control of a sample of known origin.

In one embodiment of the invention, the sample includes cells, and the indicator is combined with the sample in such a way that the indicator is added within the sample cells. By selection of the appropriate chelating moiety, fluorophore, and the substituents thereon, indicators may be prepared that will selectively localize in a desired organelle, and provide measurements of the target ion in those organelles. Conjugates of the indicators of the invention with organelle-targeting peptides may be used to localize the indicator to the selected organelle, facilitating measurement of target ion presence or concentration within the organelle (as described in U.S. Pat. No. 5,773,227, hereby incorporated by reference). Alternatively, selection of a lipophilic fluorophore, or a fluorophore having predominantly lipophilic substituents may result in localization of the indicator in lipophilic environments in the cell, such as cell membranes. Selection of cationic indicators will typically result in localization of the indicator in mitochondria.

In one embodiment of the invention, the indicator compound of the invention optionally further includes a metal ion. In another embodiment, the compounds of the invention, in any of the embodiments described above, are associated, either covalently or noncovalently, with a surface such as a microfluidic chip, a silicon chip, a microscope slide, a microplate well, or another solid or semisolid matrix, and is combined with the sample of interest as it flows over the surface. In this embodiment, the detectable optical response may therefore be detected on the matrix surface itself, typically by use of instrumental detection. This embodiment of the invention may be particularly suited to high-throughput screening using automated methods.

The fluorescence response of the indicator to the target ion may be detected by various means that include without limitation measuring fluorescence changes with fluorometers, fluorescence microscopes, laser scanners, flow cytometers, and microfluidic devices, as well as by cameras and other imaging equipment. These measurements may be made remotely by incorporation of the fluorescent ion sensor as part of a fiber optic probe. The indicator may be covalently attached to the fiber optic probe material, typically glass or functionalized glass (e.g., aminopropyl glass) or the indicator may be attached to the fiber optic probe via an intermediate polymer, such as polyacrylamide. The indicator solution is alternatively incorporated non-covalently within a fiber optic probe, as long as there is a means whereby the target ion may come into contact with the indicator solution. More preferably, the BAPTA indicators of the invention are used with a fluorescence microplate reader that is equipped with an automated liquid handling system such as FLIPR, FLEXSTATION and FDSS.

In another aspect of the invention, the fluorescent ion indicators of the invention may be used in combination with one or more non-fluorescent dyes that are not substantially cell-permeable in order to reduce the background fluorescence analogous to the methods described in U.S. Pat. No. 6,420,183, hereby incorporated by reference. Non-fluorescent dyes and dye mixtures that have large water solubilities and minimal effects on the physiology of the cells are preferred for this application. More preferably are water-soluble azo dyes (such as trypan blue), which have been used in cell-based assays for many years (H. W. Davis, R. W. Sauter. Histochemistry, 1977, 54, 177; W. E. Hathaway, L. A. Newby, J. H. Githens, Blood, 1964, 23, 517; C. W. Adams, O. B. Bayliss, R. S. Morgan, Atherosclerosis, 1977, 27, 353).

The screening methods described herein can be performed with cells growing in or deposited on solid surfaces. A common technique is to use a microwell plate where the fluorescence measurements are performing using a commercially available fluorescent plate reader. These methods lend themselves to use in high throughput screening using both automated and semi-automated systems.

Using the indicators of the present invention, the measurement of fluorescence intensity can provide a sensitive method for monitoring changes in intracellular ion concentrations. Thus, fluorescence measurements at appropriate excitation and emission wavelengths provide a fluorescence readout which is sensitive to the changes in the ion concentrations.

In one embodiment, the invention includes a) adding a compound as described above to a sample containing a cell; b) incubating the sample for a time sufficient for the compound to be loaded into the cell and an indicator compound to be generated intracellularly; c) illuminating the sample at a wavelength that generates a fluorescence response from the indicator compound; d) detecting a fluorescence response from the indicator compound; and e) correlating the fluorescence response with the presence of intracellular calcium.

In one aspect of the invention, the disclosed method is useful for screening potential therapeutic drugs, for example drugs which may affect ion concentrations in biological cells. These methods may include measuring ion concentrations as described above in the presence and absence (as a control measurement) of the test sample. Control measurements are usually performed with a sample containing all components of the test sample except for the putative drug being screened. Detection of a change in ion concentration in the presence of the test agent relative to the control indicates that the test agent is active. Ion concentrations can also be determined in the presence or absence of a pharmacologic agent of known activity (i.e., a standard agent) or putative activity (i.e., a test agent). A difference in ion concentration as detected by the methods disclosed herein allows one to compare the activity of the test agent to that of a standard agent of known activity. It will be recognized that many combinations and permutations of drug screening protocols are known to one of skill in the art and they may be readily adapted to use with the method of ion concentration measurement disclosed herein to identify compounds which affect ion concentrations.

Figure 5:
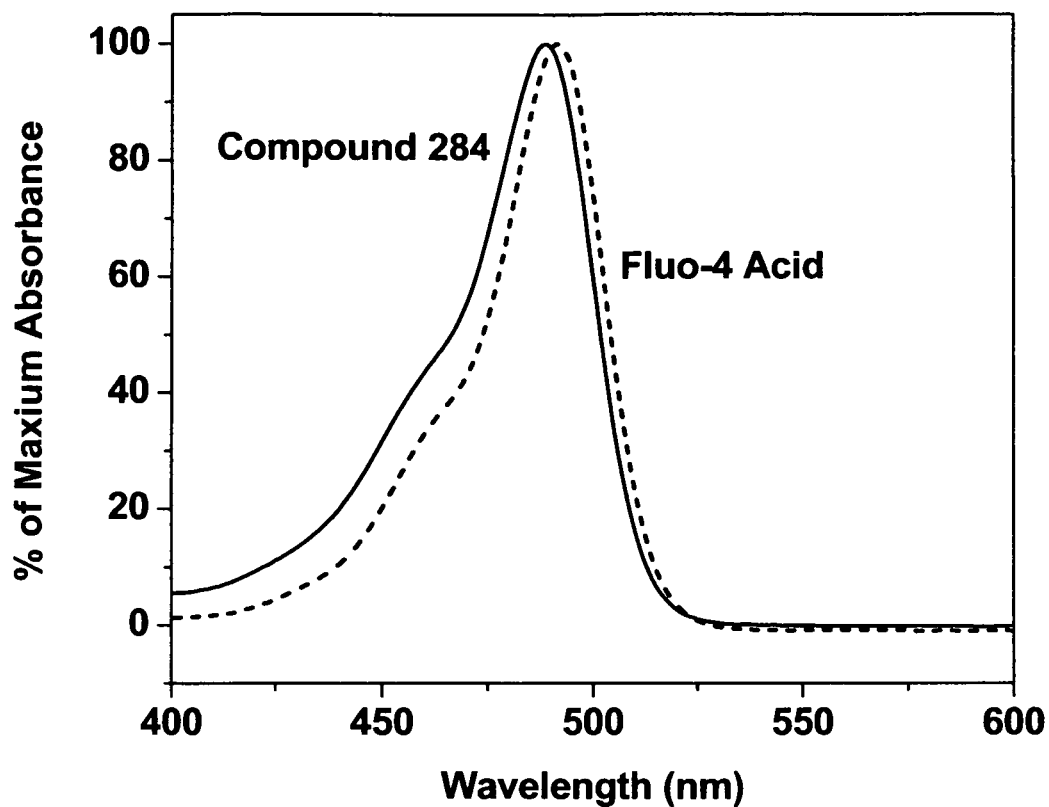
FIG. 5. The absorption spectral comparison of Fluo-4 acid and Compound 284. Fluo-4 (5 µM) and Compound 284 (5 µM) are dissolved in calcium chloride (0.1 mM)-PBS buffer (pH 7.2). The absorption spectra were normalized at their maximum absorption peak.
Figure 6:
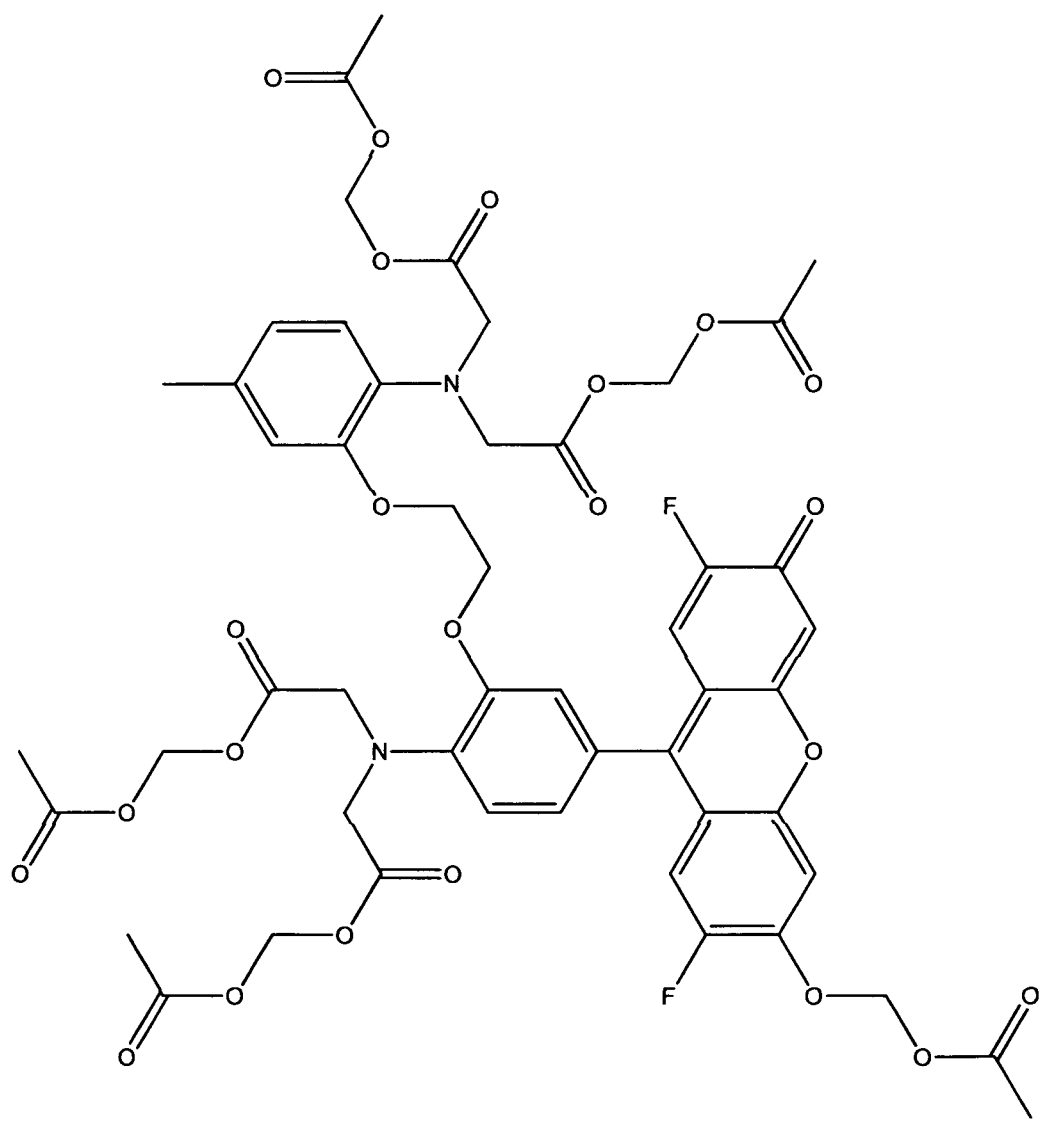
FIG. 6. Structure of Fluo-4 AM.

In one aspect of the invention, the disclosed calcium indicators have the minimal assay background in their masked form since their non-hydrolyzed AM esters cannot be excited at 488 nm, the common excitation wavelength for using fluorescein-based calcium indicators (e.g., Fluo-3 and Fluo-4). As seen from FIG. 5, Compound 306 has essentially no absorption at 488 nm while Fluo-4 AM has substantial absorption at 488 nm. Compound 306 and Fluo-4 AM are the masked form that does not bind calcium, their fluorescence caused by 488 nm excitation generates the detrimental assay background. It is evident that the calcium indicators of the invention (e.g., Compound 306) have unexpected spectral properties that enable more sensitive detection of calcium in cells compared to the existing fluorescein-based calcium indicators (such as Fluo-3 AM and Fluo-4 AM). FIG. 6 indicates that Compound 284 (the hydrolyzed product of Compound 306) binds calcium, and is well excited at 488 nm to give the fluorescence that is related to calcium concentration as well as Fluo-4.

In yet another aspect of the invention, the fluorescent ion indicators are used in a method to measure calcium flux. Cells (e.g., CHO cells) stably transfected with muscarinic receptor 1 are plated—e.g., at 60,000 cells per 100 µl per well in F12 with 5% FBS and 1% glutamine in a 96-well black wall/clear bottom Costar plate—and incubated (e.g., in 5% $CO_2$ at 37° C. overnight). The growth medium is removed and the cells are incubated with a fluorescent ion indicator (e.g., with 100 µl/well of 1-8 µM Fluo-4 AM or Compound 306 in Hanks and HEPES buffer for 1 hour at room temperature) with or without probenecid. Carbachol is added (e.g., 50 µl/well by NOVOstar, FlexStation or FLIPR) to achieve a final concentration. Fluorescent ion indicators of the invention (e.g., Compound 306) load into cells much better than Fluo-4 AM, at certain ATP concentrations (e.g., 0.1 µM, 0.2 µM, 0.3 µM, 0.4 µM, 0.5 µM, 0.6 µM, 0.7 µM, 0.8 µM, 0.9 µM, or 1.0 µM) loading more than 10%, 20%, 30%, 40%, 50%, 60%, 70%, 80%, 90% or 100% faster. When probenecid is not used, the fluorescence intensity of a fluorescent ion indicator of the invention (e.g., Compound 306), is much greater than that of Fluo-4 AM. At certain ATP concentrations (e.g., 0.1 µM, 0.2 µM, 0.3 µM, 0.4 µM, 0.5 µM, 0.6 µM, 0.7 µM, 0.8 µM, 0.9 µM, or 1.0 µM) the intensity is more than 50%, 100%, 150%, 200%, 250%, 300%, 350% or 400% greater. The calcium indicators of the invention are unexpectedly well retained inside cells compared to the existing fluorescein-based calcium indicators (such as Fluo-3 and Fluo-4) that quickly leaks out of cell, another factor resulting higher assay background besides their high 488 nm absorption (see above). When probenecid is not used, Fluo-4 AM is not capable of detecting calcium in some types of cells and tissues for which Compound 306 is used.

In yet another aspect of the invention, the disclosed method may facilitate the screening of test samples in order to identify one or more compounds that are capable of modulating the activity of an ion channel, pump or exchanger in a membrane, and the method further includes stimulating the cell, monitoring changes in the intensity of the fluorescence response from the indicator compound, and correlating the changes in fluorescence intensity with changes in intracellular calcium levels.

An additional method may be used to evaluate the efficacy of a stimulus that generates a target ion response, including (a) loading a first set and a second set of cells with the ion indicators of the invention which monitor ion concentrations; (b) optionally, exposing both the first and second set of cells to a stimulus which modulates the ion channel, pump or exchanger; (c) exposing the first set of cells to the test sample; (d) measuring the ion concentrations in the first and second sets of cells; and (e) relating the difference in ion concentrations between the first and second sets of cells to the ability of a compound in the test sample to modulate the activity of an ion channel, pump or exchanger in cells. In one aspect of the recited method, the method may include the addition of probenecid or a probenecid derivative to the sample.

One or more of the methods disclosed herein may be enhanced by the addition of a cell-impermeant and non-fluorescent dye to the sample, such that the dye remains in the extracellular solution, and acts as an acceptor dye for energy transfer from the indicator compound, thereby decreasing background signal from the sample solution. In one aspect of the method, the cell-impermeant and non-fluorescent dye is a water-soluble azo dye.

Ion channels of particular interest may include, but are not limited to, sodium, calcium, potassium, nonspecific cation, and chloride ion channels, each of which may be constitutively open, voltage-gated, ligand-gated, or controlled by intracellular signaling pathways.

Biological cells of potential interest for screening application may include, but are not limited to, primary cultures of mammalian cells, cells dissociated from mammalian tissue, either immediately or after primary culture. Cell types may include, but are not limited to white blood cells (e.g. leukocytes), hepatocytes, pancreatic beta-cells, neurons, smooth muscle cells, intestinal epithelial cells, cardiac myocytes, glial cells, and the like. The disclosed method may also include the use of recombinant cells into which ion transporters, ion channels, pumps and exchangers have been inserted and expressed by genetic engineering. Many cDNA sequences for such transporters have been cloned (see U.S. Pat. No. 5,380,836 for a cloned sodium channel, hereby incorporated by reference) and methods for their expression in cell lines of interest are within the knowledge of one of skill in the art (see, U.S. Pat. No. 5,436,128, hereby incorporated by reference). Representative cultured cell lines derived from humans and other mammals include LM cells, HEK-293 (human embryonic kidney cells), 3T3 fibroblasts, COS cells, CHO cells, RAT1 and HepG2 cells, Hela cells, $U_2OS$ cells and Jurkat cells etc.

Assay Kits

Due to the advantageous properties and the simplicity of use of the disclosed ion indicator compounds, they possess particular utility in the formulation of a kit for the complexation, detection, or quantification of selected target ions. An exemplary kit may include one or more compounds or compositions of the invention in any of the embodiments described above, either present as a pure compound, in a suitable carrier composition, or dissolved in an appropriate stock solution. The kit may further include instructions for the use of the indicator compound to complex or detect a desired target ion. The kit may further include one or more additional components, such as an additional detection reagent.

The indicator of the invention may be present in the kit associated with a surface, such as a chip, microplate well, or other solid or semi-solid matrix.

The additional kit components may be selected from, without limitation, calibration standards of a target ion, ionophores, fluorescence standards, aqueous buffers, surfactants and organic solvents. The additional kit components may be present as pure compositions, or as aqueous solutions that incorporate one or more additional kit components. Any or all of the kit components optionally further comprise buffers.

In one aspect of the disclosed kit, the kit includes at least one indicator compound as described above, and a non-fluorescent and cell-impermeant quencher dye. The non-fluorescent and cell-impermeant quencher dye is optionally present in a combined buffer solution with the compound, or the buffer solution of the cell-impermeant quencher dye is present in a separate container from the indicator compound.

The examples provided below illustrate selected aspects of the invention. They are not intended to limit or define the entire scope of the invention.

EXAMPLES
Example 1
Preparation of Compound 284
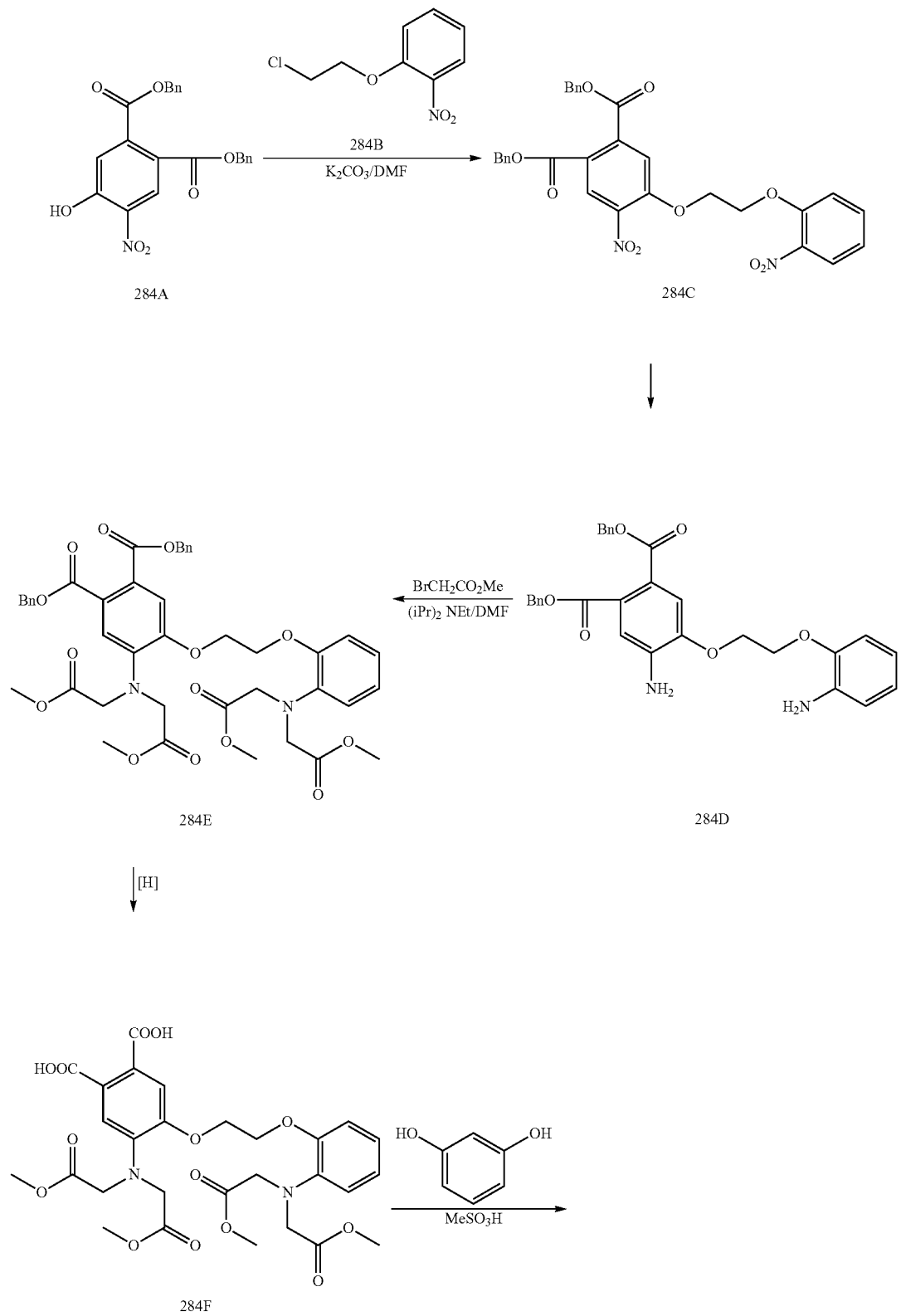

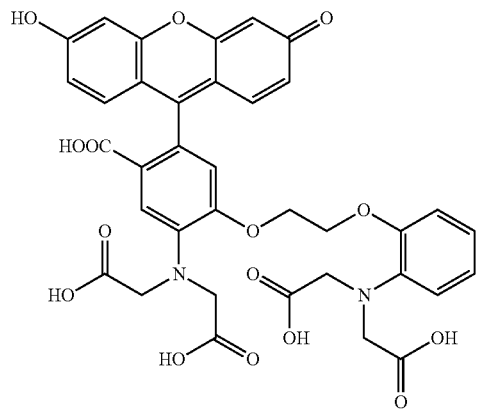

284

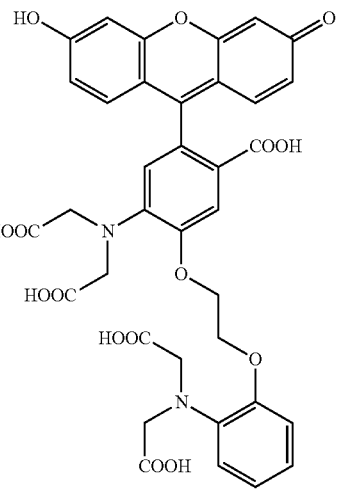

284G

Compound 284A (100 g, Shaanxi Zhendi Chemical Biology, Ltd.) is converted to Compound 284C analogously to the US Patent Application 20080254498 (Diwu et al).

Compound 284C (50 g) is dissolved in ethanol. To the ethanol solution is added 100 g stannous chloride hydrate. The reaction mixture is heated at reflux until Compound 284C is completely consumed, cooled to room temperature, and poured into ice water. The reaction mixture is neutralized with sodium carbonate to have pH=6-7, and filtered to collect the solid that is further purified on a silica gel column eluted with a gradient of chloroform/methanol to give pure Compound 284D.

Compound 248D (25 g) is dissolved in warm MeCN (100 mL) at room temperature. To the reaction mixture (iPr)$_2$NEt (80 mL) is added with stirring, and then methyl bromoacetate (50 mL) is added with stirring. The reaction mixture is refluxed until Compound 284D is completely consumed. The reaction mixture is allowed to cool to 40-60° C., poured into ethyl acetate (500 mL), and filtered to remove the white solid (the (iPr)$_2$NEt ammonium bromide salt). The combined ethyl acetate filtrates are concentrated in vacuo to give an oily solid is further purified on a silica gel column using a gradient of chloroform/methanol as eluent to give the pure off-while solid (Compound 284E).

Compound 284E (30 g) is dissolved in DMF at room temperature. To the solution 10% palladium on carbon (5 g) is added. The reaction mixture is hydrogenated until Compound 284E is completely consumed. The reaction mixture is filtered through diatomaceous earth to remove the catalyst which is washed with DMF. The combined DMF solution is poured into water. The formed solid is collected by filtration, and washed with water. The dried solid is purified on a silica gel column using a gradient of chloroform/ethyl acetate/methanol to give Compound 284F as an off-white solid.

Phthalic acid 284F (10 g) is added to the solution of resorcinol (5 g) in methanesulfonic acid (15 mL). The resulting mixture is heated under dry nitrogen at 70-80° C. until Compound 284F is completely consumed. The cooled mixture is poured into ice water followed by filtration. The reaction mixture is stirred at room temperature overnight to completely convert partially methylated Compound 284 to the free acid Compound 284. The filtrate containing Compound 284 and its isomer 284G is dried, and purified on a silica gel column eluted with a gradient of water/acetonitrile to give the mixture of Compound 284 and its isomer 284G. The mixture of Compounds 284 and 284G is further purified by HPLC using C18 column and a gradient of 0.1% TFA acetonitrile-0.1% TFA buffer to give the pure Compound 284 and 284G.

Example 2

Preparation of Compound 286

Compound 286 is prepared analogously to the procedure of Compound 284.

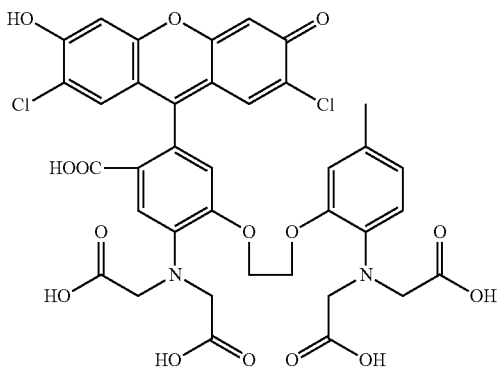

286

Example 3

Preparation of Compound 306

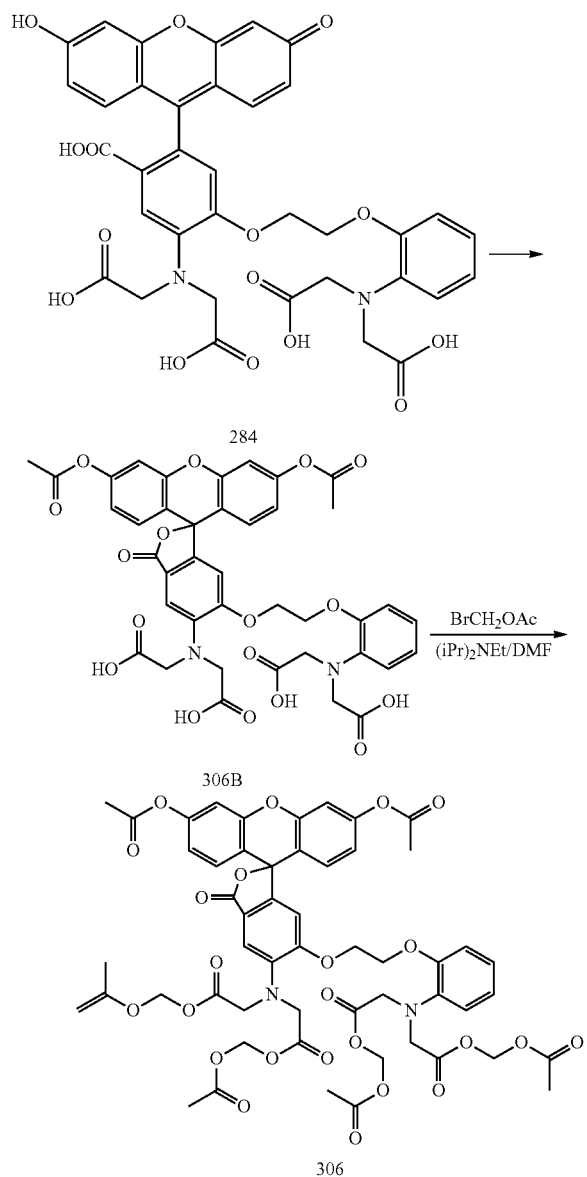

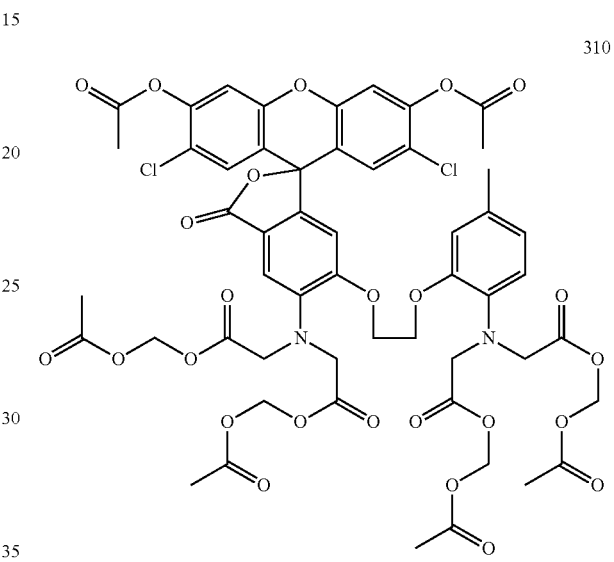

Compound 284 (350 mg) is heated at 80° C. with Ac$_2$O (5 mL) and pyridine (0.1 mL) until Compound 284 is completely consumed. The solution is cooled to room temperature. The reaction mixture is poured into ice water, and carefully adjusted to pH=4-5. The aqueous mixture is titrated with dioxane to give a precipitate that is collected by filtration. The resulting mixture is first air-dried, and further vacuum-dried in a desiccator with P$_2$O$_5$ for 12 hours to yield crude Compound 306B that is directly used for next step reaction.

The crude Compound 306B (100 mg) is dissolved in anhydrous DMF (3 mL) at room temperature. To the solution BrCH$_2$OAc (0.18 mL) was slowly added while stirring in a water bath. To the resulted mixture iPr$_2$NEt (0.38 mL) is added slowly. The reaction mixture is stirred for 24-36 hours, and concentrated in vacuo. The residue is suspended in ethyl acetate (20 mL) and stirred for 1-2 hours. The mixture is filtered to remove the solid that is washed with ethyl acetate, and the filtrate is evaporated to dryness. The filtrate residue is purified on a silica gel column using 3:1:1 hexanes/EtOAc/chloroform as an eluent to give the desired Compound 306.

Example 4

Preparation of Compound 310

Compound 310 is prepared analogously to the procedure of Compound 306.

Example 5

Preparation of Compound 315

Compound 315 is prepared analogously to the procedure of Compound 306.

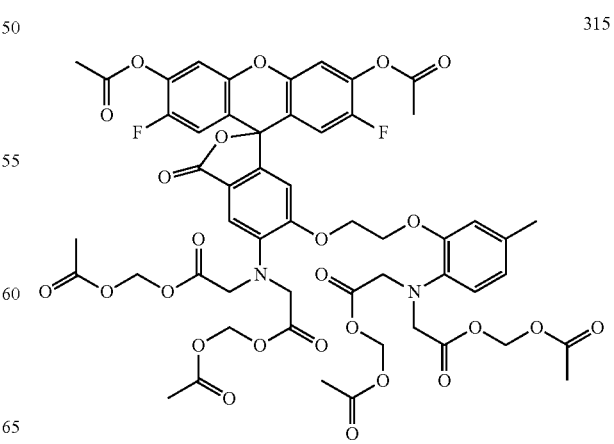

Example 6

Preparation of Compound 320

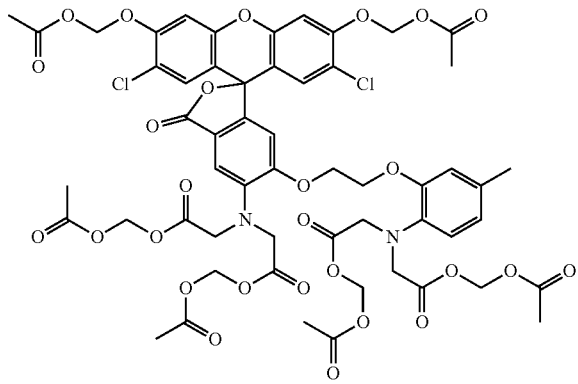 [SMILES: CC(=O)OCOC(=O)CN(CC(=O)OCOC(C)=O)c1ccc(C)cc1OCCOc1cc2c(cc1N(CC(=O)OCOC(C)=O)CC(=O)OCOC(C)=O)C(=O)OC21c2cc(F)c(OCOC(C)=O)cc2Oc2cc(OCOC(C)=O)c(F)cc21]

320

Compound 286 (100 mg) is dissolved in anhydrous DMF (3 mL) at RT. To the solution BrCH₂OAc (0.5 mL) is slowly added while stirring in a water bath. To the resulted mixture iPr₂NEt (0.38 mL) is added slowly. The reaction mixture is stirred for 24-36 hours, and concentrated in vacuo. The oily residue is purified on a silica gel column using 3:1:1 EtOAc/Hexanes/chloroform as an eluent to give the desired Compound 320.

Example 7

Preparation of Compound 325

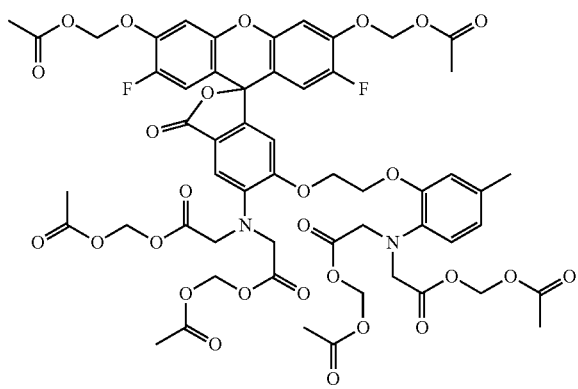

Compound 325 is prepared analogously to the procedure of Compound 320.

Example 8

Calcium Responses of the Fluorescent Indicators Measured Using a Microplate Reader Equipped with an Automated Liquid Handling System Calcium flux assays are preferred methods in drug discovery for screening G protein coupled receptors (GPCR). The fluorescent indicators of the invention provide a homogeneous fluorescence-based assay for detecting the intracellular calcium mobilization. Cells expressing a GPCR of interest that signals through calcium are pre-loaded with the indicator AM esters (such as Fluo-3 AM, Fluo-4 AM, Compounds 306, 310, 315, 320 or 325) which can cross cell membrane. Once inside the cell, the lipophilic blocking groups are cleaved by non-specific cell esterase, resulting in a negatively charged fluorescein dye that is well-retained in cells, and its fluorescence is greatly enhanced upon binding to calcium. When the sample cells are stimulated with screening compounds, the receptor triggers a release of intracellular calcium, which then greatly increases the fluorescence of the intracellular indicators. The combination of long wavelength fluorescence properties, high sensitivity, and often a >100 times increase in fluorescence upon binding with calcium makes the disclosed indicators well-suited for measurement of cellular calcium.

Figure 2:
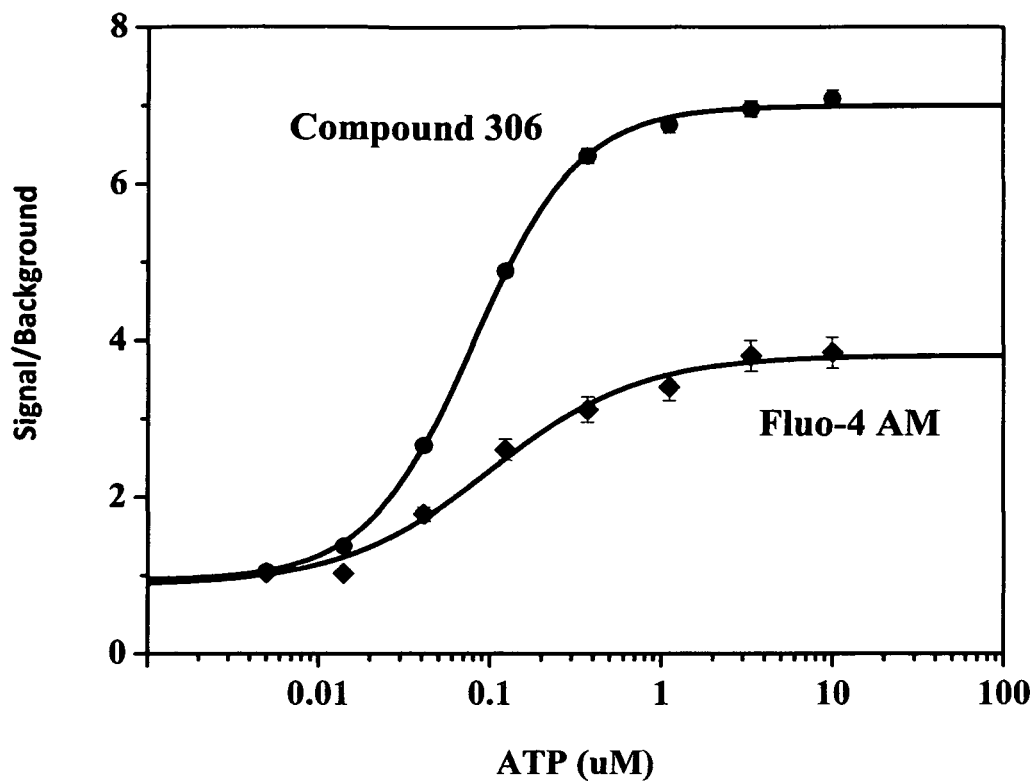
FIG. 2. Comparisons of Compound 306 and Fluo-4 AM in CHO-K1 cells in the presence of probenecid. CHO-K1 cells are seeded overnight at 50,000 cells per 100 µl per well in a 96-well black wall/clear bottom costar plate. The growth medium is removed, and the cells are incubated with 100 µl of Compound 306 and Fluo-4 AM at 5 µM in Hanks and Hepes buffer in the presence of 2.5 mM probenecid for 2 hours at 37° C., 5% $CO_2$ incubator. ATP (50 µL/well) was added by FlexStation to achieve the final desired concentrations.
Figure 3:
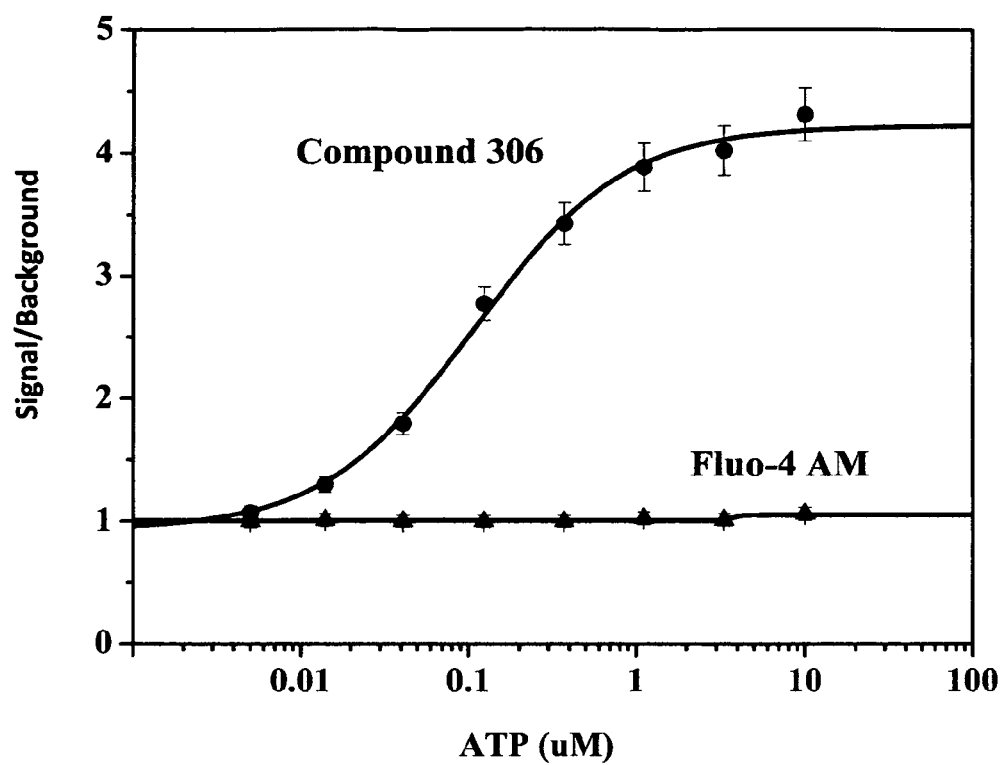
FIG. 3. Comparisons of Compound 306 and Fluo-4 AM in CHO-K1 cells in the absence of probenecid. CHO-K1 cells are seeded overnight at 50,000 cells per 100 µl per well in a 96-well black wall/clear bottom costar plate. The growth medium is removed, and the cells are incubated with 100 µl of Compound 306 and Fluo-4 AM at 5 µM in Hanks and Hepes buffer for 2 hours at 37° C. ATP (50 µL/well) is added by FlexStation to achieve the final desired concentrations.
Figure 4:
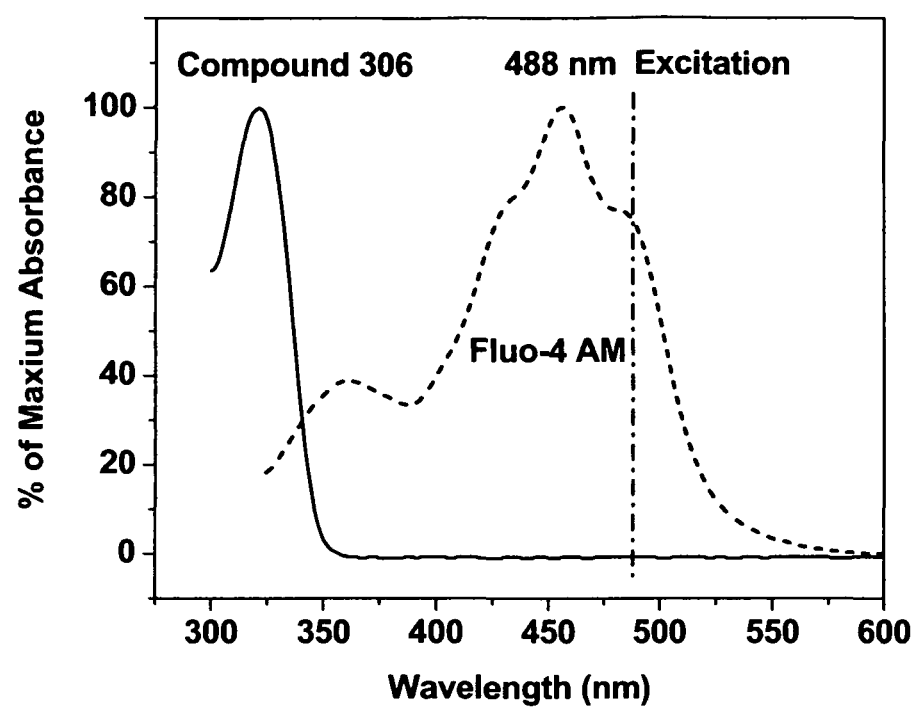
FIG. 4. The absorption spectral comparison of Fluo-4 AM and Compound 306. Fluo-4 AM (5 µM) and Compound 306 (5 µM) are dissolved in 1;1 Methanol-PBS buffer (pH 7.2). The absorption spectra were normalized at their maximum absorption peak.

Specifically, CHO cells stably transfected with muscarinic receptor 1 are plated at 60,000 cells per 100 µl per well in F12 with 5% FBS and 1% L-glutamine in a 96-well black wall/clear bottom Costar plate, incubated in 5% $CO_2$, 37° C. incubator overnight. The growth medium is removed and the cells are incubated with 100 µL/well of 1-8 µM Fluo-4 AM or Compound 306 in Hanks and HEPES buffer with 0 mM or 2.5 mM probenecid for 1 hour at room temperature. Carbachol (50 µl/well) is added by NOVOstar (BMG LabTech) or FLIPR (Molecular Devices) to achieve the final indicated concentration. A representative dose response is shown in FIGS. 2 and 3.

Compound 306 is loaded into cells much faster than Fluo-4 AM, the "gold" standard of green fluorescent calcium indicators. In addition, in the absence of probenecid Compound 306 demonstrates the unexpected better fluorescence intensity enhancement upon calcium stimulation than that of Fluo-4 AM.

Although the present invention has been shown and described with reference to the foregoing operational principles and preferred embodiments, it will be apparent to those skilled in the art that various changes in form and detail may be made without departing from the spirit and scope of the invention. The present invention is intended to embrace all such alternatives, modifications and variances that fall within the scope of the appended claims.

What is claimed is:

1. A method of detecting intracellular calcium, the method comprising:
   contacting a sample comprising a cell with a compound;
   incubating the sample for a time sufficient for the compound to be loaded into the cell and an indicator compound to be generated intracellularly;
   illuminating the sample at a wavelength that generates a fluorescence response from the indicator compound;
   detecting a fluorescence response from the indicator compound;
   wherein the compound is described by of one of the following formulas 1, 2, 3 or 4:

Formula 1

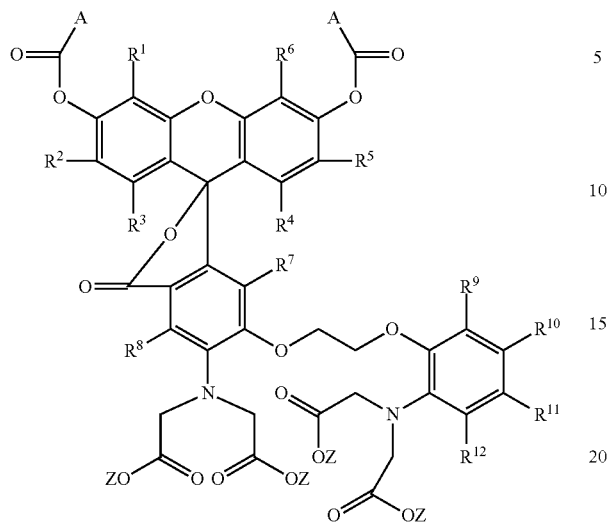

Formula 2

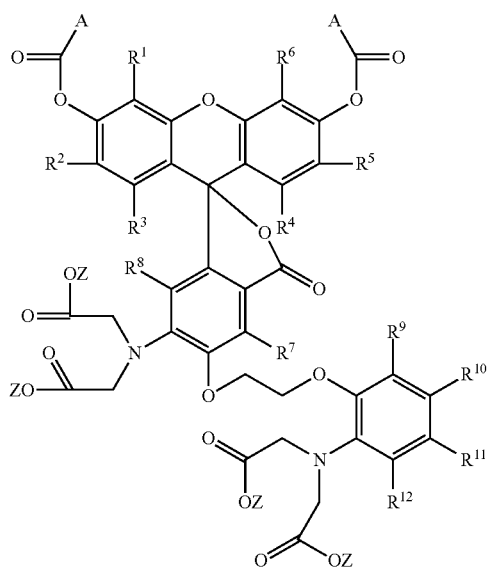

Formula 3

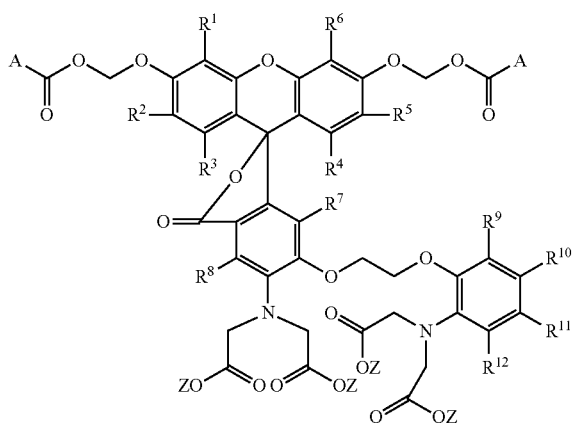

Formula 4

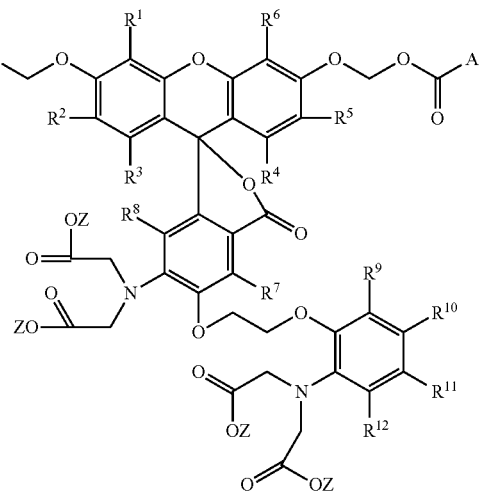

wherein $R^1$-$R^{12}$ are independently H, halogen, carboxy, alkoxy, arlyoxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; A is an alkyl having 1-10 carbons; and Z is an acyloxymethyl having 1-10 carbons.

2. The method of claim 1, wherein A is methyl and Z is acetoxymethyl.

3. The method of claim 2, wherein $R^1$ and $R^3$, $R^4$ and $R^6$-$R^8$ are each hydrogen; $R^9$-$R^{12}$ are independently hydrogen, halogen, nitro or alkyl; and $R^2$ and $R^5$ are independently hydrogen, fluoro or chloro.

4. A method of monitoring intracellular calcium comprising:
   a) contacting a sample containing a cell with a compound;
   b) incubating the sample for a time sufficient for the compound to be loaded into the cell and an indicator compound to be generated intracellularly;
   c) illuminating the sample at a wavelength that generates a fluorescence response from the indicator compound; and
   d) detecting the fluorescence response from the indicator compound;
   e) monitoring changes in the intensity of the fluorescence response from the indicator compound; and
   f) correlating the changes in fluorescence intensity with changes in intracellular calcium levels;
   wherein the compound is of one of the following formulas 1, 2, 3 or 4:

Formula 1

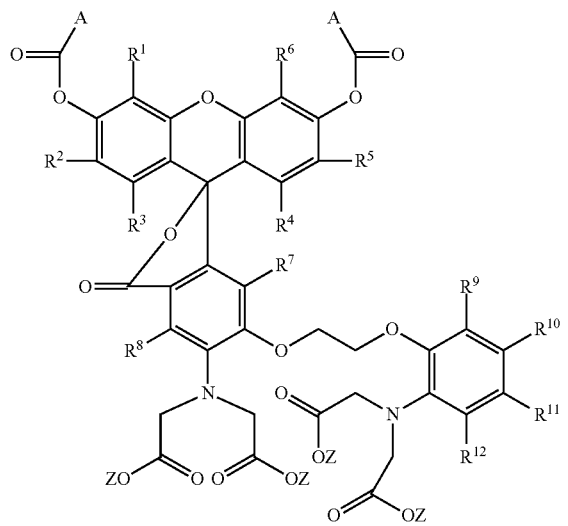

Formula 2

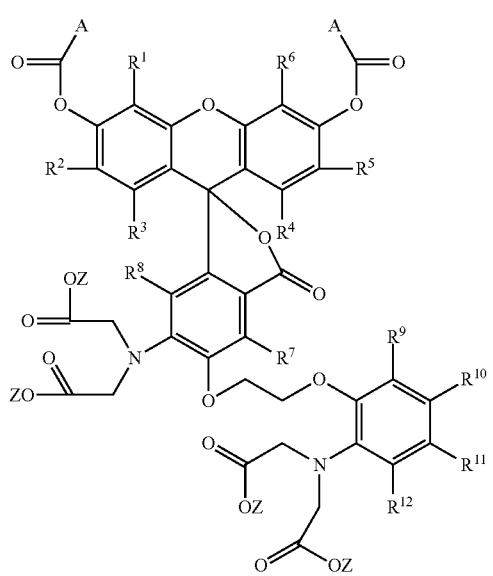

Formula 3

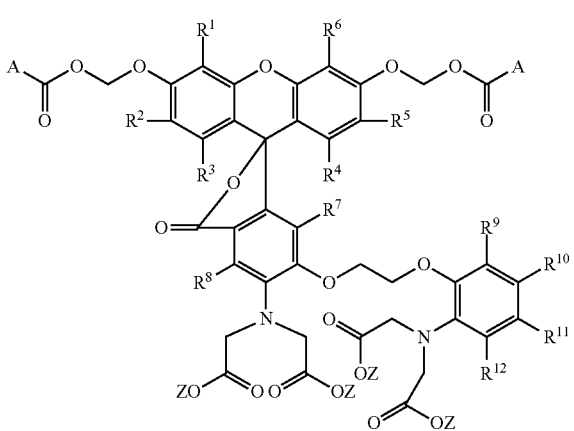

Formula 4

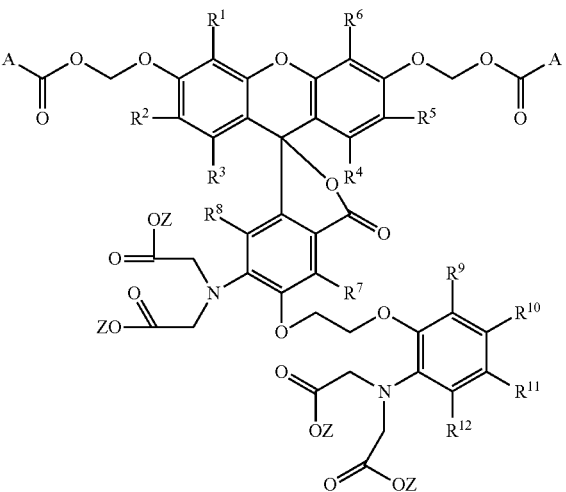

wherein $R^1$-$R^{12}$ are independently H, halogen, carboxy, alkoxy, arlyoxy, thiol, alkylthiol, arylthiol, azido, nitro, nitroso, cyano, amino, hydroxy, phosphonyl, sulfonyl, carbonyl, boronic acid, aryl or heteroaryl; or alkyl, or alkoxy that is itself optionally substituted one or more times by halogen, amino, hydroxy, phosphonyl, sulfonyl, carbonyl, boronic acid, aryl or heteroaryl; A is an alkyl having 1-10 carbons; and Z is an acyloxymethyl having 1-10 carbons.

5. The method of claim 4, further comprising stimulating the cell.

6. The method of claim 5, further comprising adding a cell-impermeant and a non-fluorescent dye to the sample.

7. The method of claim 2, wherein $R^1$ and $R^3$, $R^4$ and $R^6$-$R^{12}$ are each hydrogen; and $R^2$ and $R^5$ are independently hydrogen, fluoro or chloro.

8. The method of claim 7, wherein $R^2$ and $R^5$ are each fluoro.

9. The method of claim 7, wherein the compound is of the formula:

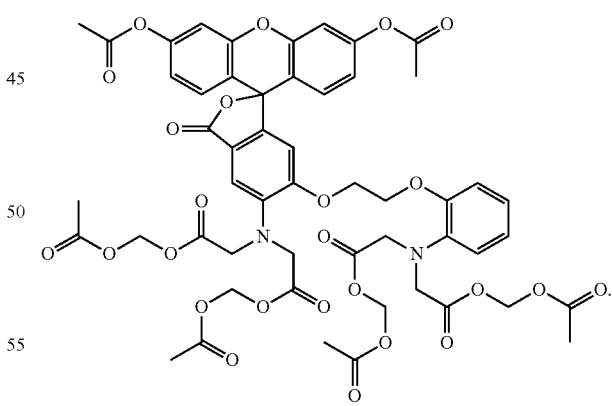

10. The method of claim 4, wherein A is methyl and Z is acetoxymethyl.

11. The method of claim 10, wherein $R^1$ and $R^3$, $R^4$ and $R^6$-$R^8$ are each hydrogen; $R^9$-$R^{12}$ are independently hydrogen halogen, nitro or alkyl; and $R^2$ and $R^5$ are independently hydrogen, fluoro or chloro.

12. The method of claim 11, wherein $R^1$ and $R^3$, $R^4$ and $R^6$-$R^{12}$ are each hydrogen; and $R^2$ and $R^5$ are independently hydrogen, fluoro or chloro.

13. The method of claim 12, wherein $R^2$ and $R^5$ are each fluoro.

14. The method of claim 12, wherein the compound is of the formula:

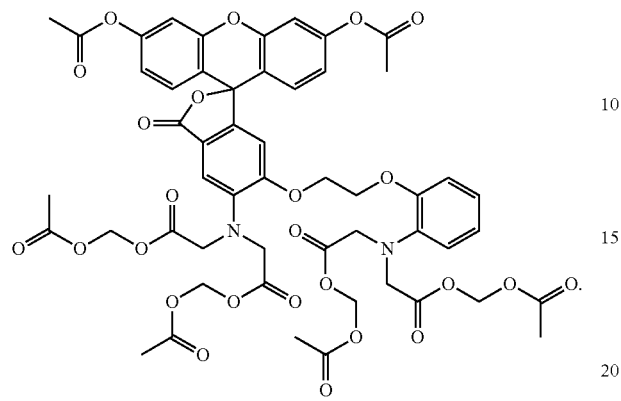

15. The method of claim 7, wherein $R^2$ and $R^5$ are each hydrogen.

16. The method of claim 3, wherein $R^{10}$ is methyl and $R^9$, $R^{11}$ and $R^{12}$ are each hydrogen.

17. The method of claim 12, wherein $R^2$ and $R^5$ are each hydrogen.

18. The method of claim 11, wherein $R^{10}$ is methyl and $R^9$, $R^{11}$ and $R^{12}$ are each hydrogen.

* * * * *